(12) United States Patent
Park et al.

(10) Patent No.: US 9,109,242 B2
(45) Date of Patent: *Aug. 18, 2015

(54) CORYNEBACTERIA HAVING ENHANCED L-LYSINE PRODUCTIVITY AND A METHOD OF PRODUCING L-LYSINE USING THE SAME

(75) Inventors: Young Hoon Park, Seongnam-si (KR); Sang Jo Lim, Incheon-si (KR); Jun Ok Moon, Seoul (KR); So Yeon Rah, Seoul (KR); Hee Jong Lee, Anyang-si (KR); Jae Woo Jang, Suwon-si (KR); Do Hyun Kwon, Ulsan-si (KR); Hyo Jin Kim, Seoul (KR); Jin Suck Sung, Yongin-si (KR); Hyung Joon Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 1145 days.

This patent is subject to a terminal disclaimer.

(21) Appl. No.: 12/441,358

(22) PCT Filed: Sep. 17, 2007

(86) PCT No.: PCT/KR2007/004478
§ 371 (c)(1),
(2), (4) Date: Mar. 13, 2009

(87) PCT Pub. No.: WO2008/033001
PCT Pub. Date: Mar. 20, 2008

(65) Prior Publication Data
US 2010/0143984 A1    Jun. 10, 2010

(30) Foreign Application Priority Data

Sep. 15, 2006   (KR) .................. 10-2006-0089672

(51) Int. Cl.
| | | |
|---|---|---|
| C12P 13/08 | (2006.01) | |
| C12N 9/02 | (2006.01) | |
| C12N 9/10 | (2006.01) | |
| C12N 9/12 | (2006.01) | |
| C12N 9/88 | (2006.01) | |

(52) U.S. Cl.
CPC ................. C12P 13/08 (2013.01); C12N 9/001 (2013.01); C12N 9/1096 (2013.01); C12N 9/1217 (2013.01); C12N 9/88 (2013.01)

(58) Field of Classification Search
CPC .................................................... C12P 13/08
See application file for complete search history.

(56) References Cited

U.S. PATENT DOCUMENTS

| | | |
|---|---|---|
| 6,200,785 B1 | 3/2001 | Kreutzer et al. |
| 6,221,636 B1 | 4/2001 | Hayakawa et al. |
| 6,740,742 B2 | 5/2004 | Mockel et al. |
| 6,746,855 B2 | 6/2004 | Kreutzer et al. |
| 6,861,246 B2 | 3/2005 | Kreutzer et al. |
| 2002/0055153 A1 | 5/2002 | Kreutzer et al. |
| 2003/0055232 A1 | 3/2003 | Li et al. |
| 2005/0255568 A1 | 11/2005 | Bailey et al. |
| 2006/0084152 A1 | 4/2006 | Pompejus et al. |

FOREIGN PATENT DOCUMENTS

| | | |
|---|---|---|
| CN | 1187540 A | 7/1998 |
| EP | 0733710 A1 | 9/1996 |
| EP | 0854189 A2 | 7/1998 |
| JP | 62-079788 A | 4/1987 |
| JP | 10-215883 A | 8/1998 |
| JP | 2001-037495 A | 2/2001 |
| JP | 2002-508921 A | 3/2002 |
| JP | 2003-503006 A | 1/2003 |
| KR | 1020050065712 A | 6/2005 |
| KR | 1020060068505 A | 6/2006 |
| WO | 2005121349 A2 | 12/2005 |
| WO | 2006/065095 A1 | 6/2006 |
| WO | 2006/071099 * | 7/2006 |
| WO | 2006/071099 A1 | 7/2006 |

OTHER PUBLICATIONS

GenBank Accession No. BA000036 (Oct. 2004).*
Contador C.A. et al., "Ensemble modeling for strain development of l-lysine-producing *Escherichia coli*," Metabolic Engineering, Jul. 1, 2009, pp. 221-233, vol. 11, No. 4-5, Academic Press.
Koffas Mattheos A.G. et al., "Effect of pyruvate carboxylase overexpression on the physiology of *Corynebacterium glutamicum*," Applied and Environmental Microbiology, Nov. 2002, pp. 5422-5428, vol. 68, No. 11.
Extended European Search Report dated Jan. 5, 2010, for European Application No. 07808268.
International Search Report dated Jan. 2, 2008, for International Application No. PCT/KR2007/004478.

* cited by examiner

*Primary Examiner* — Rebecca Prouty
(74) *Attorney, Agent, or Firm* — Seed IP Law Group PLLC

(57) ABSTRACT

A variant of *Corynebacterium* shows activity greater than the endogenous activity of aspartate aminotransferase, aspartate kinase, aspartate semialdehyde dehydrogenase, dihydrodipicolinate synthase, dihydropicolinate reductase and diaminopimelate dicarboxylase and additionally pyruvate carboxylase. The variant is used in a method of producing L-lysine.

22 Claims, 7 Drawing Sheets

SEQUENCE LISTING

<160> NUMBER OF SEQ ID NOS: 50

<210> SEQ ID NO 1
<211> LENGTH: 27
<212> TYPE: DNA
<213> ORGANISM: Artificial Sequence
<220> FEATURE:
<223> OTHER INFORMATION: forward primer for aspB amplification

<400> SEQUENCE: 1
cccggggcgg ttcagctaga gttatgc

```
<210> SEQ ID NO 2
<211> LENGTH: 27
<212> TYPE: DNA
<213> ORGANISM: Artificial Sequence
<220> FEATURE:
<223> OTHER INFORMATION: reverse primer for aspB amplification

<400> SEQUENCE: 2
aagcttttag ttagcgtaat gctccgc                                          27

<210> SEQ ID NO 3
<211> LENGTH: 27
<212> TYPE: DNA
<213> ORGANISM: Artificial Sequence
<220> FEATURE:
<223> OTHER INFORMATION: forward primer for aspB amplification

<400> SEQUENCE: 3
aagcttgcgg ttcagctaga gttatgc                                          27

<210> SEQ ID NO 4
<211> LENGTH: 27
<212> TYPE: DNA
<213> ORGANISM: Artificial Sequence
<220> FEATURE:
<223> OTHER INFORMATION: reverse primer for aspB amplification

<400> SEQUENCE: 4
gctagcttag ttagcgtaat gctccgc                                          27

<210> SEQ ID NO 5
<211> LENGTH: 30
<212> TYPE: DNA
<213> ORGANISM: Artificial Sequence
<220> FEATURE:
<223> OTHER INFORMATION: forward primer for lysCasd amplification

<400> SEQUENCE: 5
ttgcacggat cccagggtag ttgactaaag                                       30

<210> SEQ ID NO 6
<211> LENGTH: 30
<212> TYPE: DNA
<213> ORGANISM: Artificial Sequence
<220> FEATURE:
<223> OTHER INFORMATION: reverse primer for lysCasd amplification

<400> SEQUENCE: 6
atggatcccg ggtatcaacg cgtcggtaga                                       30

<210> SEQ ID NO 7
<211> LENGTH: 30
<212> TYPE: DNA
<213> ORGANISM: Artificial Sequence
<220> FEATURE:
<223> OTHER INFORMATION: forward primer for lysCasd amplification

<400> SEQUENCE: 7
ttgcaccccg ggcagggtag ttgactaaag                                       30

<210> SEQ ID NO 8
<211> LENGTH: 30
<212> TYPE: DNA
<213> ORGANISM: Artificial Sequence
<220> FEATURE:
<223> OTHER INFORMATION: reverse primer for lysCasd amplification
```

<400> SEQUENCE: 8
atggatcgat cgtatcaacg cgtcggtaga                             30

<210> SEQ ID NO 9
<211> LENGTH: 29
<212> TYPE: DNA
<213> ORGANISM: Artificial Sequence
<220> FEATURE:
<223> OTHER INFORMATION: forward primer for dapAdapB amplication

<400> SEQUENCE: 9
gacgaattct cattggcgtt tccggatcc                              29

<210> SEQ ID NO 10
<211> LENGTH: 29
<212> TYPE: DNA
<213> ORGANISM: Artificial Sequence
<220> FEATURE:
<223> OTHER INFORMATION: reverse primer for dapAdapB amplification

<400> SEQUENCE: 10
tcagagctca caagcgccaa ggaactacc                              29

<210> SEQ ID NO 11
<211> LENGTH: 29
<212> TYPE: DNA
<213> ORGANISM: Artificial Sequence
<220> FEATURE:
<223> OTHER INFORMATION: forward primer for dapAdapB amplification

<400> SEQUENCE: 11
tgagagctct cattggcgtt tccggatcc                              29

<210> SEQ ID NO 12
<211> LENGTH: 29
<212> TYPE: DNA
<213> ORGANISM: Artificial Sequence
<220> FEATURE:
<223> OTHER INFORMATION: reverse primer for dapAdapB amplification

<400> SEQUENCE: 12
tgtctcgaga caagcgccaa ggaactacc                              29

<210> SEQ ID NO 13
<211> LENGTH: 27
<212> TYPE: DNA
<213> ORGANISM: Artificial Sequence
<220> FEATURE:
<223> OTHER INFORMATION: forward primer for argSlysA amplification

<400> SEQUENCE: 13
attaagcttt gcatgggcac gtcgatg                                27

<210> SEQ ID NO 14
<211> LENGTH: 29
<212> TYPE: DNA
<213> ORGANISM: Artificial Sequence
<220> FEATURE:
<223> OTHER INFORMATION: reverse primer for argSlysA amplification

<400> SEQUENCE: 14
attgcggccg ctccacggcg aaggtgaag                              29

<210> SEQ ID NO 15
<211> LENGTH: 29
<212> TYPE: DNA
<213> ORGANISM: Artificial Sequence
<220> FEATURE:
<223> OTHER INFORMATION: forward primer for argSlysA amplification

<400> SEQUENCE: 15
attgcggccg ctgcatgggc acgtcgatg                                  29

<210> SEQ ID NO 16
<211> LENGTH: 26
<212> TYPE: DNA
<213> ORGANISM: Artificial Sequence
<220> FEATURE:
<223> OTHER INFORMATION: reverse primer for argSlysA amplification

<400> SEQUENCE: 16
attctagatc cacggcgaag gtgaag                                     26

<210> SEQ ID NO 17
<211> LENGTH: 18
<212> TYPE: DNA
<213> ORGANISM: Artificial Sequence
<220> FEATURE:
<223> OTHER INFORMATION: PRIMER

<400> SEQUENCE: 17
gcagtggact gtccctgc                                              18

<210> SEQ ID NO 18
<211> LENGTH: 20
<212> TYPE: DNA
<213> ORGANISM: Artificial Sequence
<220> FEATURE:
<223> OTHER INFORMATION: PRIMER

<400> SEQUENCE: 18
cctgcagcga aactgaactc                                            20

<210> SEQ ID NO 19
<211> LENGTH: 30
<212> TYPE: DNA
<213> ORGANISM: Artificial Sequence
<220> FEATURE:
<223> OTHER INFORMATION: PRIMER

<400> SEQUENCE: 19
catggcgagg atcccgttag aaatacgctc                                 30

<210> SEQ ID NO 20
<211> LENGTH: 30
<212> TYPE: DNA
<213> ORGANISM: Artificial Sequence
<220> FEATURE:
<223> OTHER INFORMATION: PRIMER

<400> SEQUENCE: 20
ttcacgccga attcgacaag gcaatcaccg                                 30

<210> SEQ ID NO 21
<211> LENGTH: 16
<212> TYPE: DNA
<213> ORGANISM: Artificial Sequence
<220> FEATURE:
<223> OTHER INFORMATION: PRIEMR

<400> SEQUENCE: 21
aggcatttca ttggca         16

<210> SEQ ID NO 22
<211> LENGTH: 16
<212> TYPE: DNA
<213> ORGANISM: Artificial Sequence
<220> FEATURE:
<223> OTHER INFORMATION: PRIMER

<400> SEQUENCE: 22
tttgcgtgcc gcagca         16

<210> SEQ ID NO 23
<211> LENGTH: 20
<212> TYPE: DNA
<213> ORGANISM: Artificial Sequence
<220> FEATURE:
<223> OTHER INFORMATION: PRIMER

<400> SEQUENCE: 23
gagatcagct ggtgtcatgg     20

<210> SEQ ID NO 24
<211> LENGTH: 19
<212> TYPE: DNA
<213> ORGANISM: Artificial Sequence
<220> FEATURE:
<223> OTHER INFORMATION: PRIMER

<400> SEQUENCE: 24
atccacagcg aactgggcg       19

<210> SEQ ID NO 25
<211> LENGTH: 1488
<212> TYPE: DNA
<213> ORGANISM: Corynebacterium glutamicum

<400> SEQUENCE: 25
gcggttcagc tagagttatg cgaaggatcc cgtgcggcgt ttatcttgtg aactccccca    60
gggcaggaat gcagcaaggg tcagcgagct ctgacgggtg cgcgggatcc cctaaaacgt   120
ctagagtagt ggcttgaggt cactgctctt tttttgtgcc cttttttggt ccgtctattt   180
tgccaccaca tgcggaggta cgcagttatg agttcagttt cgctgcagga ttttgatgca   240
gagcgaattg gtttgttcca cgaggacatt aagcgcaagt tgatgagct caagtcaaaa    300
aatctgaagc tggatcttac tcgcggtaag ccttcgtcgg agcagttgga tttcgctgat   360
gagttgttgg cgttgcctgg taagggtgat ttcaaggctg cggatggtac tgatgtccgt   420
aactatggcg ggctggatgg catcgttgat attcgccaga tttgggcgga tttgctgggt   480
gttcctgtgg agcaggtctt ggcggggat gcttcgagct tgaacatcat gtttgatgtg   540
atcagctggt cgtacatttt cggtaacaat gattcggttc agccttggtc gaaggaagaa   600
accgttaagt ggatttgccc tgttccgggc tatgatcgcc atttctccat cacggagcgt   660
ttcggctttg agatgatttc tgtgccaatg aatgaagacg ccctgatat ggatgctgtt    720
gaggaattgg tgaagaatcc gcaggttaag ggcatgtggg ttgttccggt gttttctaac   780
ccgactggtt tcacggtgac agaagacgtc gcaaagcgtc taagcgcaat ggaaaccgca   840
gctccggact tccgcgttgt gtgggataat gcctacgccg ttcatacgct gaccgatgaa   900
ttccctgagg ttatcgatat cgtcgggctt ggtgaggccg ctggcaaccc gaaccgtttc   960

```
tgggcgttca cttctacttc gaagatcact ctcgcgggtg cgggcgtgtc gttcttcctc    1020
acctctgcgg agaaccgcaa gtggtacacc ggccatgcgg gtatccgtgg cattggccct    1080
aacaaggtca atcagttggc tcatgcgcgt tactttggcg atgctgaggg agtgcgcgcg    1140
gtgatgcgta agcatgctgc gtcgttggct ccgaagttca acaaggttct ggagattctg    1200
gattctcgcc ttgctgagta cggtgtcgcg cagtggactg tccctgcggg cggttacttc    1260
atttcccttg atgtggttcc tggtacgcgc tctcgcgtgg ctgagttggc taaggaagcc    1320
ggcatcgcgt tgacgggtgc gggttcttct tacccgctgc gtcaggatcc ggagaacaaa    1380
aatctccgtt tggcaccgtc gctgcctcca gttgaggaac ttgaggttgc catggatggc    1440
gtggctacct gtgtgctgtt ggcagcagcg gagcattacg ctaactaa                 1488

<210> SEQ ID NO 26
<211> LENGTH: 1506
<212> TYPE: DNA
<213> ORGANISM: Corynebacterium glutamicum

<400> SEQUENCE: 26
cagggtagtt gactaaagag ttgctcgcga agtagcacct gtcacttttg tctcaaatat      60
taaatcgaat atcaatatat ggtctgttta ttggaacgcg tcccagtggc tgagacgcat     120
ccgctaaagc cccaggaacc ctgtgcagaa agaaaacact cctctggcta ggtagacaca     180
gtttattgtg gtagagttga gcgggtaact gtcagcacgt agatcgaaag gtgcacaaag     240
gtggccctgg tcgtacagaa atatggcggt tcctcgcttg agagtgcgga acgcattaga     300
aacgtcgctg aacggatcgt tgccaccaag aaggctggaa atgatgtcgt ggttgtctgc     360
tccgcaatgg gagacaccac ggatgaactt ctagaacttg cagcggcagt gaatcccgtt     420
ccgccagctc gtgaaatgga tatgctcctg actgctggtg agcgtatttc taacgctctc     480
gtcgccatgg ctattgagtc ccttggcgca gaagcccaat cttttcacggg ctctcaggct     540 ggtgtgctca ccaccgagcg ccacggaaac gcacgcattg ttgatgtcac tccaggtcgt     600
gtgcgtgaag cactcgatga gggcaagatc tgcattgttg ctggtttcca gggtgttaat     660
aaagaaaccc gcgatgtcac cacgttgggt cgtggtggtt ctgacaccac tgcagttgcg     720
ttggcagctg ctttgaacgc tgatgtgtgt gagatttact cggacgttga cggtgtgtat     780
accgctgacc cgcgcatcgt tcctaatgca cagaagctgg aaaagctcag cttcgaagaa     840
atgctggaac ttgctgctgt tggctccaag attttggtgc tgcgcagtgt tgaatacgct     900
cgtgcattca atgtgccact tcgcgtacgc tcgtcttata gtaatgatcc cggcactttg     960
attgccggct ctatggagga tattcctgtg aagaagcag tccttaccgg tgtcgcaacc    1020
gacaagtccg aagccaaagt aaccgttctg ggtatttccg ataagccagg cgaggctgcg    1080
aaggttttcc gtgcgttggc tgatgcagaa atcaacattg acatggttct gcagaacgtc    1140
tcttctgtag aagacggcac caccgacatc accttcacct gccctcgttc cgacggccgc    1200
cgcgcgatgg agatcttgaa gaagcttcag gttcagggca actggaccaa tgtgctttac    1260
gacgaccagg tcgcaaagt ctccctcgtg ggtgctggca tgaagtctca cccaggtgtt    1320
accgcagagt tcatggaagc tctgcgcgat gtcaacgtga acatcgaatt gatttccacc    1380
tctgagattc gtatttccgt gctgatccgt gaagatgatc tggatgctgc tgcacgtgca    1440
ttgcatgagc agttccagct gggcggcgaa gacgaagccg tcgtttatgc aggcaccgga    1500
cgctaa                                                              1506
```

<210> SEQ ID NO 27
<211> LENGTH: 1299
<212> TYPE: DNA
<213> ORGANISM: Corynebacterium glutamicum

<400> SEQUENCE: 27

| | | | | | |
|---|---|---|---|---|---|
| agttttaaag | gagtagtttt | acaatgacca | ccatcgcagt | tgttggtgca | accggccagg | 60 |
| tcggccaggt | tatgcgcacc | cttttggaag | agcgcaattt | cccagctgac | actgttcgtt | 120 |
| tctttgcttc | cccacgttcc | gcaggccgta | agattgaatt | ccgtggcacg | gaaatcgagg | 180 |
| tagaagacat | tactcaggca | accgaggagt | ccctcaagga | catcgacgtt | gcgttgttct | 240 |
| ccgctggagg | caccgcttcc | aagcagtacg | ctccactgtt | cgctgctgca | ggcgcgactg | 300 |
| ttgtggataa | ctcttctgct | tggcgcaagg | acgacgaggt | tccactaatc | gtctctgagg | 360 |
| tgaacccttc | cgacaaggat | tccctggtca | agggcattat | tgcgaacccct | aactgcacca | 420 |
| ccatggctgc | gatgccagtg | ctgaagccac | ttcacgatgc | cgctggtctt | gtaaagcttc | 480 |
| acgtttcctc | ttaccaggct | gtttccggtt | ctggtcttgc | aggtgtggaa | accttggcaa | 540 |
| agcaggttgc | tgcagttgga | gaccacaacg | ttgagttcgt | ccatgatgga | caggctgctg | 600 |
| acgcaggcga | tgtcggacct | tatgtttcac | caatcgctta | caacgtgctg | ccattcgccg | 660 |
| gaaacctcgt | cgatgacggc | accttcgaaa | ccgatgaaga | gcagaagctg | cgcaacgaat | 720 |
| cccgcaagat | tctcggtctc | ccagacctca | aggtctcagg | cacctgcgtc | cgcgtgccgg | 780 |
| ttttcaccgg | ccacacgctg | accattcacg | ccgaattcga | caaggcaatc | accgtggacc | 840 |
| aggcgcagga | gatcttgggt | gccgcttcag | gcgtcaagct | tgtcgacgtc | caaccccac | 900 |
| ttgcagctgc | cggcattgac | gaatccctcg | ttggacgcat | ccgtcaggac | tccactgtcg | 960 |
| acgataaccg | cggtctggtt | ctcgtcgtat | ctggcgacaa | cctccgcaag | ggtgctgcgc | 1020 |
| taaacaccat | ccagatcgct | gagctgctgg | ttaagtaaaa | accgccatt | aaaaactccg | 1080 |
| cttgagtgct | acactttaag | cggggtttta | atgtttgagg | ggcgatgggg | gtcgagcttg | 1140 |
| tgaagtggaa | ttttccacaa | gttttaagtt | tctttagcag | gggaaacact | gctgatagca | 1200 |
| ctagcgataa | agaacatgaa | aatgcaacgg | agctagcggc | cgaagcttta | gcggatgtca | 1260 |
| tttttcagtg | gaaaaactgg | gtctaccgac | gcgttgata | | | 1299 |

<210> SEQ ID NO 28
<211> LENGTH: 1422
<212> TYPE: DNA
<213> ORGANISM: Corynebacterium glutamicum

<400> SEQUENCE: 28

| | | | | | |
|---|---|---|---|---|---|
| cgcaaagctc | acacccacga | gctaaaaatt | catatagtta | agacaacatt | tttggctgta | 60 |
| aaagacagcc | gtaaaaacct | cttgctcgtg | tcaattgttc | ttatcggaat | gtggcttggg | 120 |
| cgattgttat | gcaaaagttg | ttaggttttt | tgcggggttg | tttaaccccc | aaatgaggga | 180 |
| agaaggtaac | cttgaactct | atgagcacag | gtttaacagc | taagaccgga | gtagagcact | 240 |
| tcggcaccgt | tggagtagca | atggttactc | cattcacgga | atccggagac | atcgatatcg | 300 |
| ctgctggccg | cgaagtcgcg | gcttatttgg | ttgataaggg | cttggattct | ttggttctcg | 360 |
| cgggcaccac | tggtgaatcc | ccaacgacaa | ccgccgctga | aaaactagaa | ctgctcaagg | 420 |
| ccgttcgtga | ggaagttggg | gatcgggcga | agctcatcgc | cggtgtcgga | accaacaaca | 480 |
| cgccgacatc | tgtggaactt | gcggaagctg | ctgcttctgc | tggcgcagac | ggcctttag | 540 |
| ttgtaactcc | ttattactcc | aagccgagcc | aagagggatt | gctggcgcac | ttcggtgcaa | 600 |

```
ttgctgcagc aacagaggtt ccaatttgtc tctatgacat tcctggtcgg tcaggtattc      660
caattgagtc tgataccatg agacgcctga gtgaattacc tacgattttg gcggtcaagg      720
acgccaaggg tgacctcgtt gcagccacgt cattgatcaa agaaacggga cttgcctggt      780
attcaggcga tgacccacta aaccttgttt ggcttgcttt gggcggatca ggtttcattt      840
ccgtaattgg acatgcagcc cccacagcat acgtgagtt gtacacaagc ttcgaggaag       900
gcgacctcgt ccgtgcgcgg gaaatcaacg ccaaactatc accgctggta gctgcccaag      960
gtcgcttggg tggagtcagc ttggcaaaag ctgctctgcg tctgcagggc atcaacgtag     1020
gagatcctcg acttccaatt atggctccaa atgagcagga acttgaggct ctccgagaag     1080
acatgaaaaa agctggagtt ctataaatat gaatgattcc cgaaatcgcg gccggaaggt     1140
tacccgcaag gcgggcccac cagaagctgg tcaggaaaac catctggata cccctgtctt     1200
tcaggcacca gatgcttcct ctaaccagag cgctgtaaaa gctgagaccg ccggaaacga     1260
caatcgggat gctgcgcaag gtgctcaagg atcccaagat tctcagggtt cccagaacgc     1320
tcaaggttcc cagaaccgcg agtccggaaa caacaaccgc aaccgttcca acaacaaccg     1380
tcgcggtggt cgtggacgtc gtggatccgg aaacgccaat ga                        1422
```

<210> SEQ ID NO 29
<211> LENGTH: 1787
<212> TYPE: DNA
<213> ORGANISM: Corynebacterium glutamicum

<400> SEQUENCE: 29

```
acaagcgcca aggaactacc tgcggaacgg gcggtgaagg gcaacttaag tctcatattt       60
caaacatagt tccacctgtg tgattaatcc ctagaacgga acaaactgat gaacaatcgt      120
taacaacaca gaccaaaacg gtcagttagg tatggatatc agcaccttct gaacgggtac      180
gtctagactg gtgggcgttt gaaaaactct tcgccccacg aaaatgaagg agcataatgg      240
gaatcaaggt tggcgttctc ggagccaaag gccgtgttgg tcaaactatt gtggcagcag      300
tcaatgagtc cgacgatctg gagcttgttg cagagatcgg cgtcgacgat gatttgagcc      360
ttctggtaga caacggcgct gaagttgtcg ttgacttcac cactcctaac gctgtgatgg      420
gcaacctgga gttctgcatc aacaacggca tttctgcggt tgttggaacc acgggcttcg      480
atgatgctcg tttggagcag gttcgcgact ggcttgaagg aaaagacaat gtcggtgttc      540
tgatcgcacc taactttgct atctctgcgg tgttgaccat ggtcttttcc aagcaggctg      600
cccgcttctt cgaatcagct gaagttattg agctgcacca ccccaacaag ctggatgcac      660
cttcaggcac cgcgatccac actgctcagg gcattgctgc ggcacgcaaa gaagcaggca     720
tggacgcaca gccagatgcg accgagcagg cacttgaggg ttcccgtggc gcaagcgtag     780
atggaatccc ggttcatgca gtccgcatgt ccggcatggt tgctcacgag caagttatct     840
ttggcaccca gggtcagacc ttgaccatca gcaggactc ctatgatcgc aactcatttg     900
caccaggtgt cttggtgggt gtgcgcaaca ttgcacagca cccaggccta gtcgtaggac     960
ttgagcatta cctaggcctg taaaggctca tttcagcagc gggtggaatt ttttaaaagg    1020
agcgtttaaa ggctgtggcc gaacaagtta aattgagcgt ggagttgata gcgtgcagtt    1080
cttttactcc acccgctgat gttgagtggt caactgatgt tgagggcgcg gaagcactcg    1140
tcgagtttgc gggtcgtgcc tgctacgaaa cttttgataa gccgaaccct cgaactgctt    1200
ccaatgctgc gtatctgcgc cacatcatgg aagtggggca cactgctttg cttgagcatg    1260
ccaatgccac gatgtatatc cgaggcattt ctcggtccgc gacccatgaa ttggtccgac    1320
```

| accgccattt | ttccttctct | caactgtctc | agcgtttcgt | gcacagcgga | gaatcggaag | 1380 |
| tagtggtgcc | cactctcatc | gatgaagatc | cgcagttgcg | tgaactttc  | atgcacgcca | 1440 |
| tggatgagtc | tcggttcgct | ttcaatgagc | tgcttaatgc | gctggaagaa | aaacttggcg | 1500 |
| atgaaccgaa | tgcactttta | aggaaaaagc | aggctcgtca | agcagctcgc | gctgtgctgc | 1560 |
| ccaacgctac | agagtccaga | atcgtggtgt | ctggaaactt | ccgcacctgg | aggcatttca | 1620 |
| ttggcatgcg | agccagtgaa | catgcagacg | tcgaaatccg | cgaagtagcg | gtagaatgtt | 1680 |
| taagaaagct | gcaggtagca | gcgccaactg | ttttcggtga | ttttgagatt | gaaactttgg | 1740 |
| cagacggatc | gcaaatggca | acaagcccgt | atgtcatgga | cttttaa | | 1787 |

<210> SEQ ID NO 30
<211> LENGTH: 3360
<212> TYPE: DNA
<213> ORGANISM: Corynebacterium glutamicum

<400> SEQUENCE: 30

| tgcatgggca | cgtcgatgct | gccacattga | gcggaggcaa | tatctacctg | aggtgggcat | 60 |
| tcttcccagc | ggatgttttc | ttgcgctgct | gcagtgggca | ttgataccaa | aaaggggcta | 120 |
| agcgcagtcg | aggcggcaag | aactgctact | acccttttta | ttgtcgaacg | ggcattacg  | 180 |
| gctccaagga | cgtttgtttt | ctgggtcagt | taccccaaaa | agcatataca | gagaccaatg | 240 |
| attttcatt  | aaaaaggcag | ggatttgtta | taagtatggg | tcgtattctg | tgcgacgggt | 300 |
| gtacctcggc | tagaatttct | ccccatgaca | ccagctgatc | tcgcaacatt | gattaaagag | 360 |
| accgcggtag | aggttttgac | ctcccgcgag | ctcgatactt | ctgttcttcc | ggagcaggta | 420 |
| gttgtggagc | gtccgcgtaa | cccagagcac | ggcgattacg | ccaccaacat | tgcattgcag | 480 |
| gtggctaaaa | aggtcggtca | gaaccctcgg | gatttggcta | cctggctggc | agaggcattg | 540 |
| gctgcagatg | acgccattga | ttctgctgaa | attgctggcc | caggctttt  | gaacattcgc | 600 |
| cttgctgcag | cagcacaggg | tgaaattgtg | gccaagattc | tggcacaggg | cgagactttc | 660 |
| ggaaactccg | atcacctttc | ccacttggac | gtgaacctcg | agttcgtttc | tgcaaaccca | 720 |
| accggaccta | ttcaccttgg | cggaacccgc | tgggctgccg | tgggtgactc | tttgggtcgt | 780 |
| gtgctggagg | cttccggcgc | gaaagtgacc | cgcgaatact | acttcaacga | tcacggtcgc | 840 |
| cagatcgatc | gtttcgcttt | gtcccttctt | gcagcggcga | agggcgagcc | aacgccagaa | 900 |
| gacggttatg | gcggcgaata | cattaaggaa | attgcggagg | caatcgtcga | aaagcatcct | 960 |
| gaagcgttgg | ctttggagcc | tgccgcaacc | caggagcttt | tccgcgctga | aggcgtggag | 1020 |
| atgatgttcg | agcacatcaa | atcttccctg | catgagttcg | gcaccgattt | cgatgtctac | 1080 |
| taccacgaga | actccctgtt | cgagtccggt | gcggtggaca | aggccgtgca | ggtgctgaag | 1140 |
| gacaacggca | acctgtacga | aaacgagggc | gcttggtggc | tgcgttccac | cgaattcggc | 1200 |
| gatgacaaag | accgcgtggt | gatcaagtct | gacggcgacg | cagcctacat | cgctggcgat | 1260 |
| atcgcgtacg | tggctgataa | gttctcccgc | ggacacaacc | taaacatcta | catgttgggt | 1320 |
| gctgaccacc | atggttacat | cgcgcgcctg | aaggcagcgg | cggcggcact | tggctacaag | 1380 |
| ccagaaggcg | ttgaagtcct | gattggccag | atggtgaacc | tgcttcgcga | cggcaaggca | 1440 |
| gtgcgtatgt | ccaagcgtgc | aggcaccgtg | gtcaccctag | atgacctcgt | tgaagcaatc | 1500 |
| ggcatcgatg | cggcgcgtta | ctcccctgatc | cgttcctccg | tggattcttc | cctggatatc | 1560 |
| gatctcggcc | tgtgggaatc | ccagtcctcc | gacaaccctg | tgtactacgt | gcagtacgga | 1620 |
| cacgctcgtc | tgtgctccat | cgcgcgcaag | gcagagacct | tgggtgtcac | cgaggaaggc | 1680 |

-continued

```
gcagacctat ctctactgac ccacgaccgc gaaggcgatc tcatccgcac actcggagag    1740
ttcccagcag tggtgaaggc tgccgctgac ctacgtgaac cacaccgcat tgcccgctat    1800
gctgaggaat tagctggaac tttccaccgc ttctacgatt cctgccacat ccttccaaag    1860
gttgatgagg atacggcacc aatccacaca gcacgtctgg cacttgcagc agcaacccgc    1920
cagaccctcg ctaacgccct gcacctggtt ggcgtttccg caccggagaa gatgtaacaa    1980
tggctacagt tgaaaatttc aatgaacttc ccgcacacgt atggccacgc aatgccgtgc    2040
gccaagaaga cggcgttgtc accgtcgctg gtgtgcctct gcctgacctc gctgaagaat    2100
acggaacccc actgttcgta gtcgacgagg acgatttccg ttcccgctgt cgcgacatgg    2160
ctaccgcatt cggtggacca ggcaatgtgc actacgcatc taaagcgttc ctgaccaaga    2220
ccattgcacg ttgggttgat gaagaggggc tggcactgga cattgcatcc atcaacgaac    2280
tgggcattgc cctggccgct ggtttccccg ccagccgtat caccgcgcac ggcaacaaca    2340
aaggcgtaga gttcctgcgc gcgttggttc aaaacggtgt gggacacgtg gtgctggact    2400
ccgcacagga actagaactg ttggattacg ttgccgctgg tgaaggcaag attcaggacg    2460
tgttgatccg cgtaaagcca ggcatcgaag cacacaccca cgagttcatc gccactagcc    2520
acgaagacca gaagttcgga ttctcccctgg catccggttc cgcattcgaa gcagcaaaag    2580
ccgccaacaa cgcagaaaac ctgaacctgg ttggcctgca ctgccacgtt ggttcccagg    2640
tgttcgacgc cgaaggcttc aagctggcag cagaacgcgt gttgggcctg tactcacaga    2700
tccacagcga actgggcgtt gcccttcctg aactggatct cggtggcgga tacggcattg    2760
cctataccgc agctgaagaa ccactcaacg tcgcagaagt tgcctccgac ctgctcaccg    2820
cagtcggaaa aatggcagcg gaactaggca tcgacgcacc aaccgtgctt gttgagcccg    2880
gccgcgctat cgcaggcccc tccaccgtga ccatctacga agtcggcacc accaaagacg    2940
tccacgtaga cgacgacaaa acccgccgtt acatcgccgt ggacggaggc atgtccgaca    3000
acatccgccc agcactctac ggctccgaat acgacgcccg cgtagtatcc cgcttcgccg    3060
aaggagaccc agtaagcacc cgcatcgtgg gctcccactg cgaatccggc gatatcctga    3120
tcaacgatga aatctaccca tctgacatca ccagcggcga cttccttgca ctcgcagcca    3180
ccggcgcata ctgctacgcc atgagctccc gctacaacgc cttcacacgg cccgccgtcg    3240
tgtccgtccg cgctggcagc tcccgcctca tgctgcgccg cgaaacgctc gacgacatcc    3300
tctcactaga ggcataacgc ttttcgacgc ctgaccccgc ccttcacctt cgccgtggag    3360
```

<210> SEQ ID NO 31  
<211> LENGTH: 31  
<212> TYPE: DNA  
<213> ORGANISM: Artificial Sequence  
<220> FEATURE:  
<223> OTHER INFORMATION: forward primer for pyc amplification

<400> SEQUENCE: 31

```
ggctctagaa ggattgcttt gtgcactcct g                                    31
```

<210> SEQ ID NO 32  
<211> LENGTH: 29  
<212> TYPE: DNA  
<213> ORGANISM: Artificial Sequence  
<220> FEATURE:  
<223> OTHER INFORMATION: reverse primer for pyc amplification

<400> SEQUENCE: 32

```
gaagatatcg agccttggtc tccatcttc                                       29
```

```
<210> SEQ ID NO 33
<211> LENGTH: 31
<212> TYPE: DNA
<213> ORGANISM: Artificial Sequence
<220> FEATURE:
<223> OTHER INFORMATION: forward primer for pyc amplification

<400> SEQUENCE: 33
gaagatatca ggattgcttt gtgcactcct g                              31

<210> SEQ ID NO 34
<211> LENGTH: 29
<212> TYPE: DNA
<213> ORGANISM: Artificial Sequence
<220> FEATURE:
<223> OTHER INFORMATION: reverse primer for pyc amplification

<400> SEQUENCE: 34
gacaagcttg agccttggtc tccatcttc                                 29

<210> SEQ ID NO 35
<211> LENGTH: 24
<212> TYPE: DNA
<213> ORGANISM: Artificial Sequence
<220> FEATURE:
<223> OTHER INFORMATION: PRIMER

<400> SEQUENCE: 35
ctgaggaaga gcaggcgcac ctcg                                      24

<210> SEQ ID NO 36
<211> LENGTH: 24
<212> TYPE: DNA
<213> ORGANISM: Artificial Sequence
<220> FEATURE:
<223> OTHER INFORMATION: PRIMER

<400> SEQUENCE: 36
ttccgcacac tcgcgggcaa gctg                                      24

<210> SEQ ID NO 37
<211> LENGTH: 3925
<212> TYPE: DNA
<213> ORGANISM: Corynebacterium glutamicum

<400> SEQUENCE: 37
aggattgctt tgtgcactcc tgggttttca ctttgttaag cagttttggg gaaaagtgca    60
aagtttgcaa agtttagaaa tattttaaga ggtaagatgt ctgcaggtgg aagcgtttaa   120
atgcgttaaa cttggccaaa tgtggcaacc tttgcaaggt gaaaaactgg ggcggggtta   180
gatcctgggg ggtttatttc attcactttg gcttgaagtc gtgcaggtca ggggagtgtt   240
gcccgaaaac attgagagga aaacaaaaac cgatgtttga ttgggggaat cgggggttac   300
gatactagga cgcagtgact gctatcaccc ttggcggtct cttgttgaaa ggaataatta   360
ctctagtgtc gactcacaca tcttcaacgc ttccagcatt caaaaagatc ttggtagcaa   420
accgcggcga atcgcggtc cgtgcttttcc gtgcagcact cgaaaccggt gcagccacgg   480
tagctattta cccccgtgaa gatcggggat cattccaccg ctcttttgct tctgaagctg   540
tccgcattgg taccgaaggc tcaccagtca aggcgtacct ggacatcgat gaaattatcg   600
gtgcagctaa aaaagttaaa gcagatgcca tttacccggg atacggcttc ctgtctgaaa   660
atgcccagct tgcccgcgag tgtgcggaaa acggcattac ttttattggc ccaaccccag   720
```

```
aggttcttga tctcaccggt gataagtctc gcgcggtaac cgccgcgaag aaggctggtc    780
tgccagtttt ggcggaatcc accccgagca aaaacatcga tgagatcgtt aaaagcgctg    840
aaggccagac ttaccccatc tttgtgaagg cagttgccgg tggtggcgga cgcggtatgc    900
gttttgttgc ttcacctgat gagcttcgca aattagcaac agaagcatct cgtgaagctg    960
aagcggcttt cggcgatggc gcggtatatg tcgaacgtgc tgtgattaac cctcagcata   1020
ttgaagtgca gatccttggc gatcacactg gagaagttgt acacctttat gaacgtgact   1080
gctcactgca gcgtcgtcac caaaaagttg tcgaaattgc gccagcacag catttggatc   1140
cagaactgcg tgatcgcatt tgtgcggatg cagtaaagtt ctgccgctcc attggttacc   1200
agggcgcggg aaccgtggaa ttcttggtcg atgaaaaggg caaccacgtc ttcatcgaaa   1260
tgaacccacg tatccaggtt gagcacaccg tgactgaaga agtcaccgag gtggacctgg   1320
tgaaggcgca gatgcgcttg gctgctggtg caaccttgaa ggaattgggt ctgacccaag   1380
ataagatcaa gacccacggt gcagcactgc agtgccgcat caccacggaa gatccaaaca   1440
acggcttccg cccagatacc ggaactatca ccgcgtaccg ctcaccaggc ggagctggcg   1500
ttcgtcttga cggtgcagct cagctcggtg gcgaaatcac cgcacacttt gactccatgc   1560
tggtgaaaat gacctgccgt ggttccgact ttgaaactgc tgttgctcgt gcacagcgcg   1620
cgttggctga gttcaccgtg tctggtgttg caaccaacat tggtttcttg cgtgcgttgc   1680
tgcgggaaga ggacttcact tccaagcgca tcgccaccgg attcattgcc gatcacccgc   1740
acctccttca ggctccacct gctgatgatg agcagggacg catcctggat tacttggcag   1800
atgtcaccgt gaacaagcct catggtgtgc gtccaaagga tgttgcagct cctatcgata   1860
agctgcctaa catcaaggat ctgccactgc cacgcggttc ccgtgaccgc ctgaagcagc   1920
ttggcccagc cgcgttttgct cgtgatctcc gtgagcagga cgcactggca gttactgata   1980
ccaccttccg cgatgcacac cagtcttttgc ttgcgacccg agtccgctca ttcgcactga   2040
agcctgcggc agaggccgtc gcaaagctga ctcctgagct tttgtccgtg gaggcctggg   2100
gcggcgcgac ctacgatgtg gcgatgcgtt tcctctttga ggatccgtgg gacaggctcg   2160
acgagctgcg cgaggcgatg ccgaatgtaa acattcagat gctgcttcgc ggccgcaaca   2220
ccgtgggata caccccgtac ccagactccg tctgccgcgc gtttgttaag gaagctgcca   2280
gctccggcgt ggacatcttc cgcatcttcg acgcgcttaa cgacgtctcc cagatgcgtc   2340
cagcaatcga cgcagtcctg gagaccaaca ccgcggtagc cgaggtggct atggcttatt   2400
ctggtgatct ctctgatcca aatgaaaagc tctacaccct ggattactac ctaaagatgg   2460
cagaggagat cgtcaagtct ggcgctcaca tcttggccat taaggatatg ctggtctgc   2520 ttcgcccagc tgcggtaacc aagctggtca ccgcactgcg ccgtgaattc gatctgccag   2580
tgcacgtgca cacccacgac actgcgggtg gccagctggc aacctacttt gctgcagctc   2640
aagctggtgc agatgctgtt gacggtgctt ccgcaccact gtctggcacc acctcccagc   2700
catccctgtc tgccattgtt gctgcattcg cgcacacccg tcgcgatacc ggtttgagcc   2760
tcgaggctgt ttctgacctc gagccgtact gggaagcagt gcgcggactg tacctgccat   2820
ttgagtctgg aaccccaggc ccaaccggtc gcgtctaccg ccacgaaatc ccaggcggac   2880
agttgtccaa cctgcgtgca caggccaccg cactgggcct tgcggatcgt ttcgaactca   2940
tcgaagacaa ctacgcagcc gttaatgaga tgctgggacg cccaaccaag gtcacccat   3000 cctccaaggt tgttggcgac ctcgcactcc acctcgttgg tgcgggtgtg gatccagcag   3060
actttgctgc cgatccacaa aagtacgaca tcccagactc tgtcatcgcg ttcctgcgcg   3120
```

```
gcgagcttgg taaccctcca ggtggctggc cagagccact gcgcacccgc gcactggaag    3180
gccgctccga aggcaaggca cctctgacgg aagttcctga ggaagagcag gcgcacctcg    3240
acgctgatga ttccaaggaa cgtcgcaata gcctcaaccg cctgctgttc ccgaagccaa    3300
ccgaagagtt cctcgagcac cgtcgccgct tcggcaacac ctctgcgctg gatgatcgtg    3360
aattcttcta cggcctggtc gaaggccgcg agactttgat ccgcctgcca gatgtgcgca    3420
ccccactgct tgttcgcctg gatgcgatct ctgagccaga cgataagggt atgcgcaatg    3480
ttgtggccaa cgtcaacggc cagatccgcc caatgcgtgt gcgtgaccgc tccgttgagt    3540
ctgtcaccgc aaccgcagaa aaggcagatt cctccaacaa gggccatgtt gctgcaccat    3600
tcgctggtgt tgtcaccgtg actgttgctg aaggtgatga ggtcaaggct ggagatgcag    3660
tcgcaatcat cgaggctatg aagatggaag caacaatcac tgcttctgtt gacggcaaaa    3720
tcgatcgcgt tgtggttcct gctgcaacga aggtggaagg tggcgacttg atcgtcgtcg    3780
tttcctaaac ctttctgtaa aaagccccgc gtcttcctca tggaggaggc ggggcttttt    3840
gggccaagat gggagatggg tgagttggat ttggtctgat tcgacacttt taagggcaga    3900
gatttgaaga tggagaccaa ggctc                                          3925
```

```
<210> SEQ ID NO 38
<211> LENGTH: 17
<212> TYPE: DNA
<213> ORGANISM: Artificial Sequence
<220> FEATURE:
<223> OTHER INFORMATION: PRIMER

<400> SEQUENCE: 38
gggcgaattc tgcagat                                                    17

<210> SEQ ID NO 39
<211> LENGTH: 17
<212> TYPE: DNA
<213> ORGANISM: Artificial Sequence
<220> FEATURE:
<223> OTHER INFORMATION: PRIMER

<400> SEQUENCE: 39
atctgcagaa ttcgccc                                                    17

<210> SEQ ID NO 40
<211> LENGTH: 21
<212> TYPE: DNA
<213> ORGANISM: Artificial Sequence
<220> FEATURE:
<223> OTHER INFORMATION: PRIMER

<400> SEQUENCE: 40
aaacgccaat gagagctctc a                                               21

<210> SEQ ID NO 41
<211> LENGTH: 21
<212> TYPE: DNA
<213> ORGANISM: Artificial Sequence
<220> FEATURE:
<223> OTHER INFORMATION: PRIMER

<400> SEQUENCE: 41
cttggcgctt gtgagctctg a                                               21
```

<210> SEQ ID NO 42
<211> LENGTH: 25
<212> TYPE: DNA
<213> ORGANISM: Artificial Sequence
<220> FEATURE:
<223> OTHER INFORMATION: PRIMER

<400> SEQUENCE: 42
tctagaagaa acatcccagc gctac                                          25

<210> SEQ ID NO 43
<211> LENGTH: 24
<212> TYPE: DNA
<213> ORGANISM: Artificial Sequence
<220> FEATURE:
<223> OTHER INFORMATION: PRIMER

<400> SEQUENCE: 43
catatggagt gtttcctttc gttg                                           24

<210> SEQ ID NO 44
<211> LENGTH: 318
<212> TYPE: DNA
<213> ORGANISM: Corynebacterium ammoniagenes CJHB100

<400> SEQUENCE: 44
agaaacatcc cagcgctact aatagggagc gttgaccttc cttccacgga ccggtaatcg    60
gagtgcctaa aaccgcatgc ggcttaggct ccaagatagg ttctgcgcgg ccgggtaatg   120
catcttcttt agcaacaagt tgaggggtag gtgcaaataa gaacgacata gaaatcgtct   180
cctttctgtt tttaatcaac atacaccacc acctaaaaat tccccgacca gcaagttcac   240
agtattcggg cacaatatcg ttgccaaaat attgtttcgg aatatcatgg gatacgtacc   300
caacgaaagg aaacactc                                                 318

<210> SEQ ID NO 45
<211> LENGTH: 301
<212> TYPE: DNA
<213> ORGANISM: Corynebacterium ammoniagenes CJHB100

<400> SEQUENCE: 45
caccgcgggc ttattccatt acatggaatg accaggaatg cagggaatg cgacgaaatt     60 gactgtgtcg ggagcttctg atccgatgct gccaaccagg agagaaaata atgacatgtg   120
caggcacgct ggtgagctgg agatttatga tctcaagtac cttttttctt gcactcgagg   180
gggctgagtg ccagaatggt tgctgacacc aggttgaggt tggtacacac tcaccaatcc   240
tgccgtcgcg ggcgcctgcg tggaacataa accttgagtg aaacccaatc taggagatta   300
a                                                                   301

<210> SEQ ID NO 46
<211> LENGTH: 285
<212> TYPE: DNA
<213> ORGANISM: Corynebacterium ammoniagenes CJHB100

<400> SEQUENCE: 46
aattccacca gacgttgttt agtaagtgcc cgaattctcg gttggtgcag ttgcttttcg    60
atgaatggga gaacctcgaa tacttccgcg tctctacttt ccggtacgtg ccacacagag   120
cagagcaatc ggtggaagag cacgacagat tagtagcgct tatcgaagcc caggcagaag   180

```
atttctacat cgaatcccaa gcccgcaacc accgcctgac aaccgcaacg acctaccgcc    240
aacgtttaaa ttccgaaaat catcacgaag aacaaggagt gcaca                   285
```

<210> SEQ ID NO 47
<211> LENGTH: 291
<212> TYPE: DNA
<213> ORGANISM: Corynebacterium ammoniagenes CJHB100

<400> SEQUENCE: 47

```
gctgcctaca tctggacttc tgacctgaag cgctcccaca acttcgcgca aaacgttgaa    60
gccggcatgg tctggttgaa ctccaacaac gtccgtgacc tgcgcacccc attcggtggc    120
gtcaaggcat ccgtctgggc gcatgagggc ggctaccgct ccattgactt ctacaccgac    180
caacaggccg tacacatcaa cttaggcgaa gtccacaacc cagtcttcgg caagcaaacc    240
aactaattct ccctcatcca cactcccctt ttaacctcac taggagtcat c             291
```

<210> SEQ ID NO 48
<211> LENGTH: 312
<212> TYPE: DNA
<213> ORGANISM: Corynebacterium ammoniagenes CJHB100

<400> SEQUENCE: 48

```
actgggaggg tagggtcac gctgaattag caggtcacat cctgttgctt gagctggccg     60
ttaccctcct aggatccgag atgattcttg tagaggacta acgtccgcac aaatcttccg    120
cgggatgctc aaatcaccct agctggtttt gaaaaatccg tggcataaat ctaggatcgt    180
gtaactggca cgaaaagaaa gcgtcatcgg cgcttgggaa catcttttta agatattcct    240
caagtgccgt gacatctgtc aaccccgtgg ctgcgagagt cgtagtcaca atgaagtcca    300
ggaggacata ca                                                        312
```

<210> SEQ ID NO 49
<211> LENGTH: 249
<212> TYPE: DNA
<213> ORGANISM: Corynebacterium ammoniagenes CJHB100

<400> SEQUENCE: 49

```
tcggacatat acggatttac ctgctgcaat cgcgccggcc cttgctcgaa attgcgtgaa    60
ttttagtctg attgtgttgg aatatccgca gaatgtgtgg gtttgctttt ataaatctgc    120
gcagtgtagg gaacctcggt actatcggca gtgtcggaga aacttcctcg atataaatct    180
ttgaagtaat tctcccaggc aatagctttt gacgtactcc gcttcccaac ttttaggag    240 acaactacc                                                            249
```

<210> SEQ ID NO 50
<211> LENGTH: 332
<212> TYPE: DNA
<213> ORGANISM: Corynebacterium ammoniagenes CJHB100

<400> SEQUENCE: 50

```
ggcttcatcg tcgtctttga tccgatgcga gtccattaac ccaaactcct aaagcccgt     60 aaaacggggg tattccaaca cggttatcca cagtttaacc gttattcggg ggtaatccta    120
acccaaatca ttacggaaac tccaatctgg ctcacaatat cctccatgat tctagggaca    180
cccaatcagg tgcacccgct tcctgcgaca acgagtcaaa ctcggcaaag ccctcaacct    240
```

```
gtcggtctag aatatatata ccgcccggtc tagtgttgtg gtgtacacta acgataaacc    300
aacaaagttg tctattaaga ggaggccatt tc                                 332
```

CORYNEBACTERIA HAVING ENHANCED L-LYSINE PRODUCTIVITY AND A METHOD OF PRODUCING L-LYSINE USING THE SAME

This application is U.S. National Phase of International Application PCT/KR2007/004478, filed Sep. 17, 2007 designating the U.S., and published in English as WO 2008/033001 on Mar. 20, 2008, which claims priority to Korean Patent Application No. 10-2006-0089672, filed Sep. 15, 2006.

TECHNICAL FIELD

The present invention relates to a variant of *Corynebacterium* which shows activity greater than the endogenous activity of aspartate aminotransferase, aspartate kinase, aspartate semialdehyde dehydrogenase, dihydrodipicolinate synthase, dihydropicolinate reductase and diaminopimelate decarboxylase and additionally pyruvate carboxylase, and a method of producing L-lysine using the same.

BACKGROUND ART

*Corynebacterium*, especially, *Corynebacterium glutamicum*, is a Gram-positive microorganism which is widely used in the production of L-amino acids. Of L-amino acids, L-lysine is applicable in a variety of industries, including animal feedstuff, pharmaceutical and cosmetic industries. For use in these industries, typically, L-lysine is produced by fermentation using *Corynebacterium* strains.

*Corynebacterium* strains anchoring enhanced genes involved in lysine biosynthesis and methods of producing L-lysine are well known in the art. For example, U.S. Pat. No. 6,746,855 discloses *corynebacteria* strains with an enhanced lysE gene (lysine export carrier gene), to which genes selected from the group comprising a dapA gene, a lysC gene, a pyc gene and a dapB gene are additionally introduced, and a method for the production of L-lysine by cultivating the strains. U.S. Pat. No. 6,221,636 discloses a coryneform bacterium carrying a recombinant DNA comprising a DNA sequence coding for aspartokinase, in which the feedback inhibitory activity of L-lysine and L-threonine is substantially desensitized, and a DNA sequence coding for a diaminopimelate decarboxylase.

Nowhere are *Corynebacterium* spp. which show higher activity of the six enzymes involved in the biosynthesis pathway of lysine, that is, aspartate aminotransferase, aspartate kinase, aspartate semialdehyde dehydrogenase, dihydrodipicolinate synthase, dihydropicolinate reductase, and diaminopimelate decarboxylase, than the endogenous activity thereof, mentioned in any document published prior to the present invention. Furthermore, *Corynebacterium* spp. that show more than the endogenous activity of pyruvate carboxylase in addition to the six enzymes are not found in any documents published prior to the present invention.

DISCLOSURE OF INVENTION

Technical Problem

It is an object of the present invention to provide strains of *Corynebacteria* that have higher than endogenous activity of the six enzymes involved in the pathway of lysine biosynthesis, that is, aspartate aminotransferase, aspartate kinase, aspartate semialdehyde dehydrogenase, dihydrodipicolinate synthase, dihydropicolinate reductase and diaminopimelate decarboxylase.

It is another object of the present invention to provide strains of *Corynebacteria* that have higher than endogenous activity of pyruvate carboxylase, in addition to the six enzymes.

It is another object of the present invention to provide a method of producing L-lysine using the microorganisms.

Technical Solution

In order to accomplish the above objects, the present invention provides a strain of *Corynebacteria* anchoring aspartate aminotransferase, aspartate kinase, aspartate semialdehyde dehydrogenase, dihydrodipicolinate synthase, dihydropicolinate reductase and diaminopimelate decarboxylase which show higher than their respective endogenous activities.

In accordance with another aspect thereof, there is provided a strain of *Corynebacteria* in which the activity of pyruvate carboxylase is higher than the endogenous activity thereof, in addition to the six enzymes.

In accordance with a further aspect, there is provided a method of producing L-lysine using the microorganisms.

The *Corynebacteria* strains of the present invention show activities of the seven enzymes at higher levels than their endogenous levels. The elevated enzyme activity in accordance with the present invention is based on various factors including an increase in the number of gene copies, the replacement of native promoters with more potent promoters, and artificial mutation directed to activity enhancement. In greater detail, the number of gene copies can be increased by the introduction of an exogenous allele and/or by the amplification of the endogenous gene. As for the substitution of the gene promoter, examples thereof include the introduction of an exogenous promoter having potent activity to express the structural genes downstream thereof and replacement with an endogenous gene promoter. Gene amplification may be readily achieved using a method well known in the art, for example, by culturing under suitable conditions.

In accordance with an aspect of the present invention, the Coryneform bacteria of the present invention features the presence of at least one copy of aspB (a gene encoding aspartate aminotransferase), lysC (a gene encoding aspartate kinase), asd (a gene encoding aspartate semialdehyde dehydrogenase), dapA (a gene encoding dihydrodipicolinate synthase), dapB (a gene encoding dihydrodipicolinate reductase) and lysA (a gene encoding diaminopimelate dicarboxylate) in addition to the endogenous genes aspB, lysC, asd, dapA, dapB and lysA in the nuclear DNA thereof. In a modification of this aspect, potent exogenous promoters may be located upstream of the initiation codon of the respective structural genes.

In accordance with another aspect of the present invention, the coryneform bacteria of the present invention feature the presence of at least one copy of a pyc (pyruvate carboxylase) gene in addition to the endogenous pyc gene in the nuclear DNA thereof, with at least one copy of aspB, lysC, asd, dapA, dapB and lysA located therein. In a modification of this aspect, a potent exogenous promoter is located upstream of the initiation codon of the pyc gene while potent exogenous promoters replace endogenous promoters of the six respective genes.

As long as it belongs to *Corynebacterium*, any coryneform bacteria can be used as a mother strain into which the genes are introduced. Examples of *Corynebacterium* microorganisms useful in the present invention include *Corynebacterium* glutamicum ATCC13032, *Corynebacterium glutamicum*, *Corynebacterium thermoaminogenes* FERM BP-1539, *Brevibacterium flavum* ATCC 14067, *Brevibacterium lactofermentum* ATCC 13869, and L-amino acid-producing mutants or strains derived therefrom, such as *Corynebacterium glutamicum* KFCC10881 and *Corynebacterium glutamicum* KFCC11001, with preference for *Corynebacterium glutamicum* KFCC10881.

In the *Corynebacteria* microorganisms of the present invention, aspB, lysC, asd, dapA, dapB, lysA and pyc have nucleotide sequences of SEQ ID NOS.: 25, 26, 27, 28, 29, 30 and 37, respectively, each comprising a native promoter and a termination codon.

The *Corynebacteria* microorganisms of the present invention may be coryneform bacteria into which vectors pDZ-2aspB, pDZ-2lysC/asd, pDZ-2dapA/dapB, pDZ-2lysA and pDZ-2pyc, respectively having the cleavage maps of FIGS. 2 to 6, are transformed. These vectors may be introduced in a predetermined order or simultaneously. As mentioned above, respective exogenous promoters may be located upstream of the initiation codon of the genes. Preferably, the microorganism anchors at least one additional respective copy of aspB, lysC, asd, dapA, dapB, lysA and pyc in the genomic DNA thereof. In an alternative or a more preferable embodiment, a potent exogenous promoter is inserted between an initiation codon and an endogenous promoter for each gene. The insertion of an exogenous gene into genomic DNA can be achieved using a method well known in the art, for example, homologous recombination.

Particularly useful in the present invention is *Corynebacterium glutamicum* KFCC-1008 CJ4, with accession number KCCM10770P. This strain can be derived from *Corynebacterium glutamicum* KFCC-10881 by introducing pDZ-2aspB, pDZ-2 lysC/asd, pDZ-2dapA/dapB and pDZ-2lysA, respectively having the cleavage maps of FIGS. 2 to 5, and culturing the transformant in a selection medium to allow the exogenous genes aspB, lysC, asd, dapA, dapB and lysA to undergo homologous recombination with respective endogenous alleles, thereby anchoring two copies of aspB, lysC, asd, dapA, dapB and lysA in the genomic DNA thereof. This strain can produce L-lysine at higher efficiency than the mother strain. The L-lysine production efficiency can be further increased by the additional introduction of the vector pDZ-2pyc, having the cleavage map of FIG. 6, into the transformed strain so as to anchor two copies of pyc in the genomic DNA.

In accordance with another aspect thereof, the present invention provides a method of producing L-lysine at a high yield, comprising the insertion of an exogenous promoter between a native promoter and an initiation codon for individual genes.

In an embodiment of the present invention, the promoters of the lysine biosynthesis genes are replaced with respective exogenous potent CJ7 promoters. The CJ7 promoter useful in the present invention is a potent promoter, having the nucleotide sequence of SEQ ID NO. 44, derived from *Corynebacterium ammoniagenes*, which was previously developed by the present applicant (Korean Pat. No. KR-0620092). Upon the expression of lysC of *Corynebacterium glutamicum* KFCC-10881, the CJ7 promoter was found to increase the activity of aspartate kinase twice as much as the endogenous promoter. Although only examples with the CJ7 promoter are given herein, it should be understood that the CJ1 to CJ6 promoters, disclosed in Korean Pat. No. KR-0620092, respectively having nucleotide sequences of SEQ ID NOS.: 45 to 50 derived from *Corynebacterium ammoniagenes*, can be applied to the preparation of lysine-producing strains in the same manner as that used for the CJ7 promoter. Accordingly, the CJ1 to CJ6 promoters, as well as the CJ7 promoter, fall within the range of the exogenous promoter useful for increasing the expression level of genes of interest in accordance with the present invention.

In accordance with a further aspect thereof, the present invention provides a method for producing L-lysine, comprising:

culturing the microorganism of the present invention to express L-lysine within the cells or release L-lysine into a medium; and recovering L-lysine from the cells or the medium.

The culturing step is further explained below.

The microorganism in the L-lysine production method according to the present invention is as described hereinbefore.

For the culturing step, one of various processes well known in the art can be adopted. The *Corynebacteria* strain can be cultured in a batch process or a continuous process, such as a fed batch process or a repeated fed batch process.

For use in culturing, a medium must meet the requirements of the strain to be cultured. Culture media for *Corynebacteria* spp. are well known (e.g., Manual of Methods for General Bacteriology. American Society for Bacteriology. Washington D.C., USA, 1981). Examples of carbon sources useful for culturing include saccharides and carbohydrates, such as glucose, saccharose, lactose, fructose, maltose, starch, cellulose and the like, oils and lipids, such as soybean oil, sunflower oil, castor oil, coconut oil and the like, fatty acids such as palmitic acid, stearic acid, linoleic acid and the like, alcohols such as glycerols, ethanol and the like, and organic acids such as acetic acid. These materials may be used alone or in combination. The nitrogen source useful in the culture medium for the bacteria of the present invention may be represented by peptone, yeast extract, broth, malt extract, a corn steep solid, soybean flour, urea, and inorganic compounds such as ammonium sulfate, ammonium chloride, ammonium phosphate, ammonium carbonate and ammonium nitrate. These nitrogen sources may be used alone or in combination. Potassium dihydrogen phosphate or dipotassium hydrogen phosphate or sodium salts thereof can be used as a nitrogen source in the culture medium. Also, the culture medium requires a metal salt, such as magnesium sulfate or iron sulfate, as an essential ingredient for the growth of the microorganism. In addition, other essential ingredients, such as amino acids and vitamins, are contained in the culture medium. Instead of the ingredients themselves, their precursors may be used. The ingredients may be added to a culture of the microorganism in a batch manner or a continuous manner.

The pH of the culture may be adjusted with a basic compound such as sodium hydroxide, potassium hydroxide or ammonia, or an acidic compound such as phosphoric acid or sulfuric acid. A defoaming agent such as fatty acid polyglycol ester may be added to prevent the formation of bubbles. An aerobic state may be maintained by injecting oxygen or oxygen-containing gas (e.g., air) into the culture. While the organism is cultured, the culture medium is maintained within the range from 20 to 45° C. and preferably within the range from 25 to 40° C. The culturing is continued until the production of L-amino acid reaches the maximum. In this regard, it takes 10 to 160 hours to attain the maximal amount of L-lysine. This amino acid may be released into the culture medium or may remain within the cells.

The recovering step is carried out as follows. The recovery of L-lysine from cells or culture media is well known in the art. Examples of L-lysine recovery methods include, but are not limited to, filtration, anion exchange chromatography, crystallization and HPLC.

Advantageous Effects

Having higher enzyme activity than the endogenous activity of aspartate amino-transferase, aspartate kinase, aspartate semialdehyde dehydrogenase, dihydrodipicolinate synthase, dihydropicolinate reductase and diaminopimelate decarboxylase, and additionally pyruvate carboxylase, the *Corynebacteria* microorganisms of the present invention can produce L-lysine at higher yield.

Accordingly, the method featuring the use of the *Corynebacteria* microorganisms can be applied for the high-yield production of L-lysine.

BEST MODE FOR CARRYING OUT THE INVENTION

A better understanding of the present invention may be obtained through the following examples which are set forth to illustrate, but are not to be construed as the limit of the present invention.

EXAMPLE 1

Construction of Vector pDZ for Nuclear-Targeted Gene and Insertion of Gene Using the Same On the basis of the *E. coli* cloning vector pACYC177 (New England Biolab, GenBank accession # X06402), a recombinant vector pDZ for carrying a *Corynebacterium* chromosome was constructed as follows.

Figure 1:
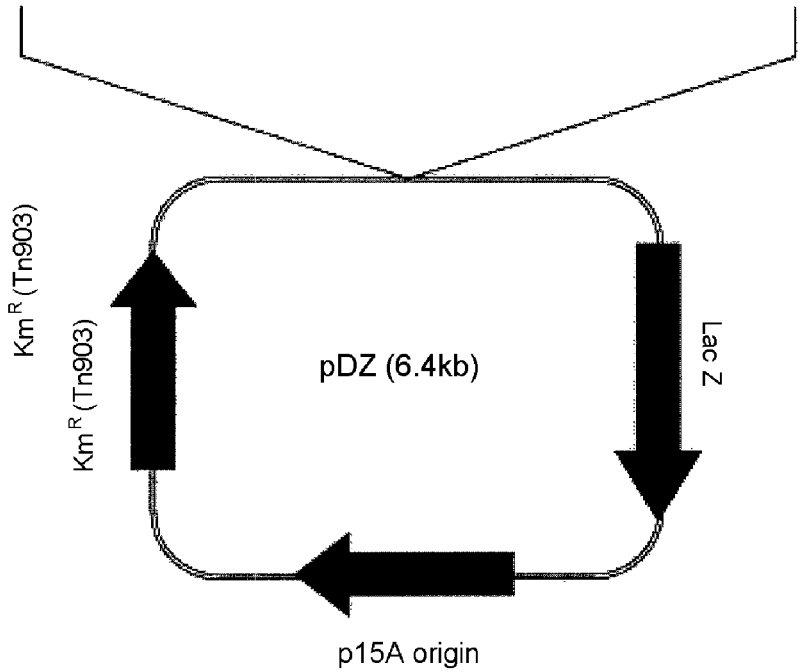
FIG. 1 is a schematic view showing a vector pDZ for a nuclear-targeted gene into *Corynebacterium*.

A digest of a pACYC177 vector resulting from treatment with AcuI and BanI restriction enzymes was blunt-ended using a Klenow enzyme. For use as a selection marker, a lacZ gene from *E. coli* was prepared by gene amplification from the nuclear DNA of *E. coli* K12 W3110 through PCR, designed to contain the promoter thereof, and then by 5' end phosphorylation and blunt end generation with T4 DNA polymerase and polynucleotide kinase. These two DNA fragments were ligated to each other to give a circular DNA molecule, followed by inserting an artificially synthesized adaptor sequence containing a plurality of restriction sites into the restriction site BamHI of the circular DNA molecule to construct the vector pDZ for nuclear-targeted gene into *Corynebacterium*. FIG. 1 is a schematic view showing the map of the vector pDZ for nuclear-targeted gene into *Corynebacterium*.

Afterwards, a gene of interest was inserted into the nuclear DNA of *Corynebacterium*. To this end, *Corynebacterium glutamicum* KFCC10881, an L-lysine-producing strain, was transformed with the pDZ vector carrying two copies of a gene of interest in tandem by electroporation (using an electrical pulse method according to *Appl. Microbiol. Biotechnol.* (1999) 52:541-545) and screened for transformants, in which the gene of interest was inserted into the chromosome due to homology on a selection medium containing 25 mg/L of kanamycin. The appearance of a blue color on the solid medium containing X-gal (5-bromo-4-chloro-3-indolyl-β-D-galactoside) indicated successful gene insertion into nuclear DNA using the vector. The primary nuclear-inserted strains were cultured in a nutrient broth (30° C., 8 hrs) with shaking and were then serially diluted from 10-4 to 10-10 before being spread on solid media containing X-gal. Most of the colonies that were grown were stained a blue color. White colonies, which were a minority of the grown colonies, were selected. These secondarily selected strains did not carry the inserted vector sequence in the genome thereof because it was removed from the genome by crossover. These strains were finally tested for susceptibility to kanamycin and analyzed for gene structure through PCR before final selection.

EXAMPLE 2

Preparation of Lysine-Producing *Corynebacterium glutamicum* (KFCC-10881) by Mutation A strain into which the genes responsible for the pathway of lysine biosynthesis were to be inserted was based on *Corynebacterium glutamicum* (KFCC-10881), which is resistant to S-(2-aminoethyl) cysteine (hereinafter referred to as "AEC") and is homoserine-leaky.

The mutant strain KFCC-10881 was prepared from the wild-type *Corynebacterium glutamicum* (ATCC13032). A medium containing the mother strain at a concentration of $10^7 \sim 10^8$ cells/ml was treated with 500 µg/ml of the mutagen N-methyl-N'-nitro-N-nitrosoguanidine (hereinafter referred to as "NTG") at 30° C. for 30 min, followed by the selection of colonies grown on a complex plate containing 5 g/l of AEC. After the primary mutant strain was analyzed for ACE resistance and lysine productivity, it was led to secondary mutation with NTG. A plurality of the colonies thus formed were tooth-picked into minimal media, which were or were not supplemented with homoserine so as to separate homoserine auxotrophs (secondary mutants), which cannot grow in a minimal medium lacking homoserine. The homoserine auxotroph was allowed to undergo tertiary mutation so as to create a homoserine-leaky strain which was identified by incubation in a minimal medium containing 10 mg/L of homoserine. The strain grown in the medium was examined for lysine productivity (Table 1). The resulting lysine-producing strain, which is AEC resistant and homoserine-leaky, was deposited with the Korean Federation of Culture Collection under the accession number of KFCC-10881. The minimal medium and the production medium used in this example are as follows.

TABLE 1

| Strains | Lysine (g/l) | | |
| --- | --- | --- | --- |
| | Batch 1 | Batch 2 | Batch 3 |
| Wild-Type (ATCC13032) | 0 | 0 | 0 |
| KFCC-10881 | 45 | 43 | 42.5 |

Minimal Medium (pH 7.0)

Glucose 100 g, $(NH_4)_2SO_4$ 40 g, Soy Protein 2.5 g, Corn Steep Solids 5 g, Urea 3 g, $KH_2PO_4$ 1 g, $MgSO_4$ $7H_2O$ 0.5 g, Biotin 100☐, Thiamine chloride 1000☐, Calcium pantothenate 2000☐, nicotinamide 3000☐, $CaC_3O$ 30 g (in 1 liter of distilled water)

Production Medium (pH 7.0)

Glucose 100 g, $(NH_4)_2SO_4$ 40 g, Soy Protein 2.5 g, Corn Steep Solids 5 g, Urea 3 g, $KH_2PO_4$ 1 g, $MgSO_4$ $7H_2O$ 0.5 g, Biotin 100☐, Thiamine chloride 1000☐, $CaC_3O$ 30 g (in 1 liter of distilled water)

EXAMPLE 3

Cloning of Lysine-Producing *Corynebacterium glutamicum* KFCC-10881-Derived aspB Gene, Construction of Recombinant Vector (pDZ-2aspB) and Preparation of Strain Anchoring aspB PCR was performed on the aspB gene involved in the pathway of lysine biosynthesis, with the nuclear DNA of the lysine-producing PCR *Corynebacterium glutamicum* KFCC10881 prepared in Example 2 serving as a template. Information on the base sequence (NCBI Registration No. NC_003450, Ncg10237) of the aspB gene was acquired from the data of the NIH GenBank and was used to design two pairs of primers to amplify an aspB gene ranging from the promoter region to the terminator codon (Table 2).

TABLE 2

| Primers | Base Sequences | SEQ ID NO. |
| --- | --- | --- |
| F-aspB-SmaI_P1 | ccc ggg gcg gtt cag cta gag tta tgc | 1 |
| R-aspB-HindIII_P2 | aag ctt tta gtt agc gta atg ctc cgc | 2 |
| F-aspB-HindIII_P3 | aag ctt gcg gtt cag cta gag tta tgc | 3 |
| R-aspB-NheI_P4 | gct agc tta gtt agc gta atg ctc cgc | 4 |

Figure 2:
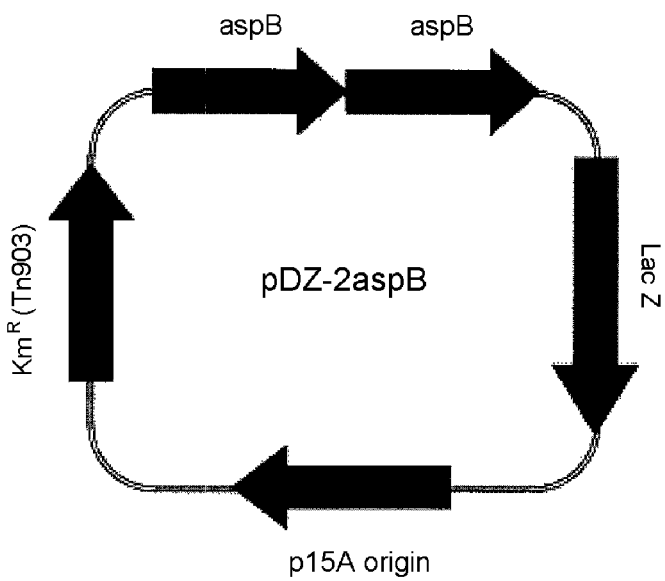
FIG. 2 is a schematic view showing a vector pDZ-2aspB for a nuclear-targeted gene into *Corynebacterium*.

PCR was performed using the nuclear DNA of *Corynebacterium glutamicum* KFCC10881 as a template and a set of oligonucleotide SEQ ID NOS. 1 and 2 or oligonucleotide SEQ ID NOS. 3 and 4 as primers in the presence of PfuUltra™ High-Fidelity DNA Polymerase (Stratagene), with 30 cycles of denaturing at 96° C. for 30 sec, annealing at 53° C. for 30 sec, and extending at 72° C. for 2 min. The PCR products thus obtained were found to be two kinds of aspB genes (aspB-A and aspB-B), each containing a 1,493 bp-long promoter region, which were produced respectively with a set of SEQ ID NOS. 1 and 2 and a set of SEQ ID NOS. 3 and 4. The PCR products were cloned into the *E. coli* vector pCR2.1 with the aid of a TOPO Cloning Kit (Invitrogen) to give recombinant vectors pCR-aspB-A and pCR-aspB-B. These pCR vectors were treated respectively with the restriction enzymes which are specific for opposite ends of aspB-A and aspB-B (aspB-A: SmaI+HindIII, aspB-B: HindIII+NheI) to separate the aspB genes from the pCR vectors. These fragments were cloned through 3-piece ligation into the EcoRV-NheI sites of a pDZ vector to produce a recombinant vector pDZ-2aspB, in which two copies of aspB were cloned in tandem. FIG. 2 is a map of a pDZ-2aspB vector for a nuclear-targeted gene into *Corynebacterium*.

The recombinant vector pDZ-2aspB was transformed into the lysine-producing *Corynebacterium glutamicum* KFCC-10881 prepared in Example 2, followed by the insertion of an additional copy of the aspB gene just next to the aspB gene in the nuclear DNA through crossover so as to produce a lysine-producing strain anchoring two copies of an aspB gene, which was named *Corynebacterium glutamicum* KFCC10881-CJ1. The adjacent positioning of two copies of the aspB gene was demonstrated by PCR using a set of primers, SEQ ID NOS. 17 and 18 (Table 3), designed to amplify the contact region between the two copies of the aspB gene.

TABLE 3

| Primers | Base Sequences | SEQ ID NOS. |
| --- | --- | --- |
| F-M-aspB | gca gtg gac tgt ccc tgc | 17 |
| R-M-aspB | cct gca gcg aaa ctg aac tc | 18 |

EXAMPLE 4

Cloning of Lysine-Producing *Corynebacterium glutamicum* KFCC-10881-Derived lysC/asd Gene, Construction of Recombinant Vector (pDZ-2lysC/asd) and Preparation of Strain Anchoring lysC/asd Information on the base sequence (NCBI Registration No. NC_003450, Ncg10247~0248) of the lysC/asd gene was acquired from data of the NIH GenBank and was used to design two pairs of primers to amplify an aspB gene ranging from the promoter region to the terminator codon (Table 4) in a manner similar to that of Example 3.

TABLE 4

| Primers | Base Sequences | SEQ ID NOS. |
| --- | --- | --- |
| lysC-F1 (BamHI) | ttg cac gga tcc cag ggt agt tga cta aag | 5 |
| asd-R1 (SmaI) | atg gat ccc ggg tat caa cgc gtc ggt aga | 6 |
| lysC-F2 (SmaI) | ttg cac ccc ggg cag ggt agt tga cta aag | 7 |
| asd-R2 (PvuI) | atg gat cga tcg tat caa cgc gtc ggt aga | 8 |

PCR was performed using the nuclear DNA of *Corynebacterium glutamicum* KFCC10881 as a template and a set of oligonucleotide SEQ ID NOS. 1 and 2 or oligonucleotide SEQ ID NOS. 3 and 4 as primers in the presence of PfuUltra™ High-Fidelity DNA Polymerase (Stratagene), with 30 cycles of denaturing at 96° C. for 30 sec, annealing at 52° C. for 30 sec, and extending at 72° C. for 3 min.

The PCR products thus obtained were found to be two kinds of lysC/asd genes, lysC/asd-A and lysC/asd-B, each containing a 2,805 bp-long promoter region, which were produced respectively with a set of SEQ ID NOS. 5 and 6 and a set of SEQ ID NOS. 7 and 8. The PCR products were cloned into the *E. coli* vector pCR2.1 with the aid of a TOPO Cloning Kit (Invitrogen) to give recombinant vectors pCR-lysC/asd-A and pCR-lysC/asd-B.

Figure 3:
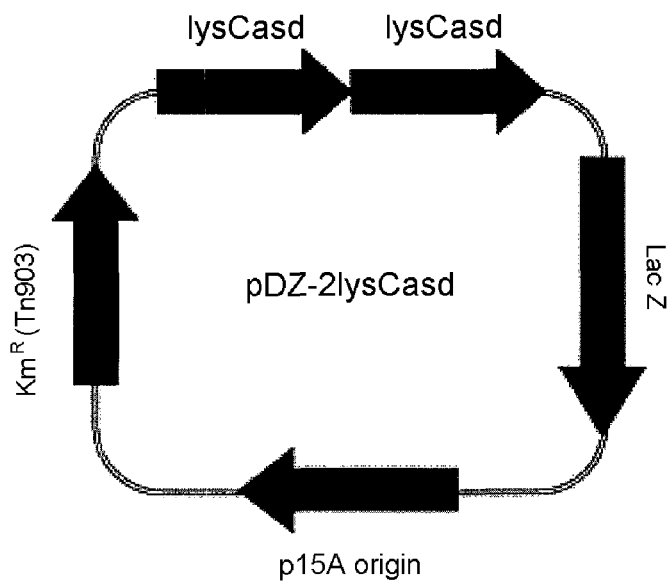
FIG. 3 is a schematic view showing a vector pDZ-2lysC/asd for a nuclear-targeted gene into *Corynebacterium*.

These pCR vectors were treated respectively with restriction enzymes that are specific for opposite ends of lysC/asd-A and lysC/asd-B (lysC/asd-A: BamHI+SmaI, lysC/asd-B: SmaI+PvuI) to separate the lysC/asd genes from the pCR vectors. These fragments were cloned through 3-piece ligation into the BamHI-PvuI sites of a pDZ vector to construct a recombinant vector pDZ-2lysC/asd in which 2 copies of lysC/asd were cloned in tandem. FIG. 3 is a map of the pDZ-2lysC/asd vector for a nuclear-targeted gene into *Corynebacterium*.

The recombinant vector pDZ-2lysC/asd was transformed into the lysine-producing *Corynebacterium glutamicum* KFCC10881-CJ1 prepared in Example 3, followed by the insertion of an additional copy of lysC/asd gene just near the lysC/asd gene in the nuclear DNA through crossover so as to produce a lysine-producing strain anchoring two copies of lysC/asd gene, which was named *Corynebacterium glutamicum* KFCC10881-CJ2. The adjacent positioning of two copies of aspB gene was identified through PCR using a set of primers (Table 5) designed to amplify the contact region between the two copies of aspB gene.

TABLE 5

| Primers | Base Sequences | SEQ ID NOS. |
|---|---|---|
| lysC-2 | cat ggc gag gat ccc gtt aga aat acg ctc | 19 |
| asd-1 | ttc acg ccg aat tcg aca agg caa tca ccg | 20 |

EXAMPLE 5

Cloning of Lysine-Producing *Corynebacterium glutamicum* KFCC-10881-Derived dapA/dapB Gene, Construction of Recombinant Vector (pDZ-2dapA/dapB) and Preparation of Strain Anchoring dapA/dapB Information on the base sequence (NCBI Registration No. NC_003450, Ncg11896~1898) of dapA/dapB gene was acquired from data of the NIH GenBank. The dapA gene was determined to comprise a dapB gene and an operon with a function-unknown ORF (Ncg1987) located therebetween. The information was used to design two pairs of primers to amplify the overall dapB-ORF (Ncg11897)-dapA gene ranging from the dapB promoter to the terminator codon (Table 6).

TABLE 6

| Primers | Base Sequences | SEQ ID NOS. |
|---|---|---|
| Dap-EcoRI-F | gac gaa ttc tca ttg gcg ttt ccg gat cc | 9 |
| Dap-Sac I-R | tca gag ctc aca agc gcc aag gaa cta cc | 10 |
| Dap-SacI-F | tga gag ctc tca ttg gcg ttt ccg gat cc | 11 |
| Dap-XhoI-R | tgt ctc gag aca agc gcc aag gaa cta cc | 12 |

PCR was performed using the nuclear DNA of *Corynebacterium glutamicum* KFCC10881 as a template and a set of oligonucleotide SEQ ID NOS. 9 and 10 or oligonucleotide SEQ ID NOS. 11 and 12 as primers in the presence of PfuUltra™ High-Fidelity DNA Polymerase (Stratagene), with 30 cycles of denaturing at 96° C. for 30 sec, annealing at 52° C. for 30 sec and extending at 72° C. for 3 min.

The PCR products thus obtained were found to be two kinds of dapA/dapB genes, dapA/dapB-A, dapA/dapB-B, each containing a 3,210 bp-long promoter region, which were produced respectively with a set of SEQ ID NOS. 9 and 10 and a set of SEQ ID NOS. 11 and 12. The PCR products were cloned into the *E. coli* vector pCR2.1 with the aid of the TOPO Cloning Kit (Invitrogen) to give recombinant vectors pCR-dapA/dapB-A and pCR-dapA/dapB-B.

Figure 4:
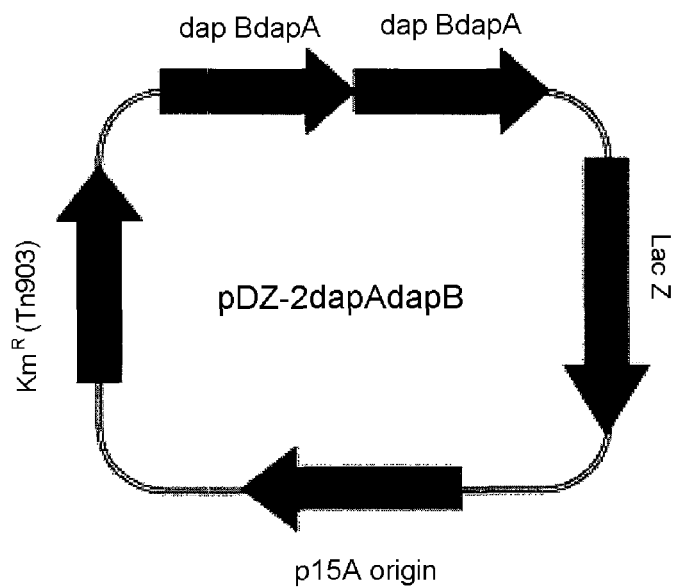
FIG. 4 is a schematic view showing a vector pDZ-2dapA/dapB for a nuclear-targeted gene into *Corynebacterium*.

These pCR vectors were treated with corresponding restriction enzymes, which are specific for opposite ends of dapA/dapB-A and dapA/dapB-B (dapA/dapB-A: EcoRI+SacI, dapA/dapB-B: SacI+XhoI) to separate the dapA/dapB genes from the pCR vectors. These fragments were cloned through 3-piece ligation into the EcoRI-XhoI sites of a pDZ vector to construct a recombinant vector pDZ-2dapA/dapB in which 2 copies of dapA/dapB were cloned in tandem. FIG. 4 is a map of the pDZ-2dapA/dapB vector.

The recombinant vector pDZ-2dapA/dapB was transformed into the lysine-producing *Corynebacterium glutamicum* KFCC10881-CJ2 prepared in Example 4, followed by the insertion of an additional copy of dapA/dapB gene just next to the dapA/dapB gene in the nuclear DNA through crossover so as to produce a lysine-producing strain anchoring two copies of the dapA/dapB gene, which was named *Corynebacterium glutamicum* KFCC10881-CJ3. The adjacent positioning of two copies of dapA/dapB gene was identified by PCR using a set of primers (Table 7) designed to amplify a contact region between the two copies of dapA/dapB gene.

TABLE 7

| Primers | Base Sequences | SEQ ID NOS. |
|---|---|---|
| Dap-seq-3 | agg cat ttc att ggc a | 21 |
| Dap-seq-5 | ttt gcg tgc cgc agc a | 22 |

EXAMPLE 6

Cloning of Lysine-Producing *Corynebacterium glutamicum* KFCC-10881-Derived lysA Gene, Construction of Recombinant Vector (pDZ-2lysA) and Preparation of Strain Anchoring lysA Information on the base sequence (NCBI Registration No. NC_003450, Ncg11132~1133) of lysA gene was acquired from data of the NIH GenBank. The lysA gene was analyzed to comprise an argS gene (arginyl-tRNA synthetase) and an operon. The information was used to design two pairs of primers to amplify the overall argS-lysA gene ranging from the argS promoter to the terminator codon (Table 8).

TABLE 8

| Primers | Base Sequences | SEQ ID NOS. |
|---|---|---|
| FargHN1 | ATT AAG CTT TGC ATG GGC ACG TCG ATG | 13 |
| RargHN1 | ATT GCG GCC GCT CCA CGG CGA AGG TGA AG | 14 |
| FargNX2 | ATT GCG GCC GCT GCA TGG GCA CGT CGA TG | 15 |
| RargNX2 | ATT CTA GAT CCA CGG CGA AGG TGA AG | 16 |

PCR was performed using the nuclear DNA of *Corynebacterium glutamicum* KFCC10881 as a template and a set of oligonucleotide SEQ ID NOS. 13 and 14 or SEQ ID NOS. 15 and 16 as primers in the presence of PfuUltra™ High-Fidelity DNA Polymerase (Stratagene), with 30 cycles of denaturing at 96° C. for 30 sec, annealing at 52° C. for 30 sec and extending at 72° C. for 4 min.

The PCR products thus obtained were found to be two kinds of argS/lysA genes, argS/lysA-A and argS/lysA-B, each containing a 3,359 bp-long promoter region, which were produced respectively with a set of SEQ ID NOS. 13 and 14 and a set of SEQ ID NOS. 15 and 16. The PCR products were cloned into the *E. coli* vector pCR2.1 with the aid of a TOPO Cloning Kit (Invitrogen) to give recombinant vectors pCR-argS/lysA-A and pCR-argS/lysA-B.

Figure 5:
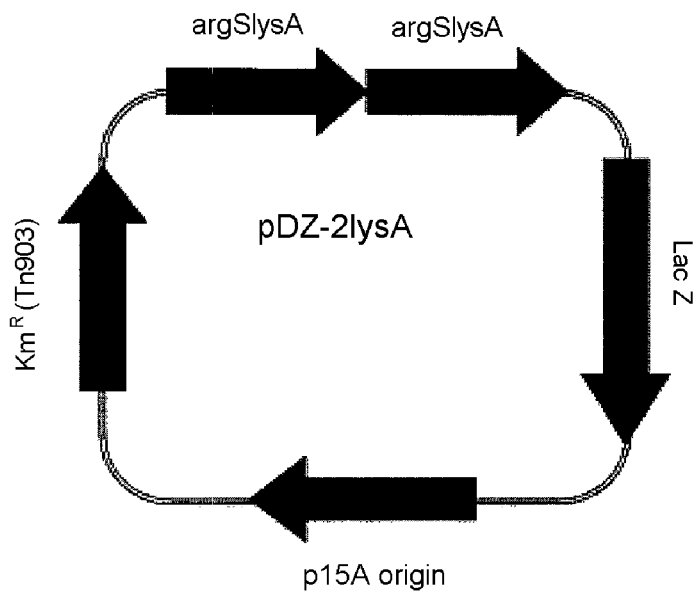
FIG. 5 is a schematic view showing a vector pDZ-2lysA for a nuclear-targeted gene into *Corynebacterium*.

These pCR vectors were treated with corresponding restriction enzymes which are specific for opposite ends of argS/lysA-A and argS/lysA-B (argS/lysA-A: HindIII+NotI, argS/lysA-B: NotI+XbaI) to separate the argS/lysA genes from the pCR vectors. These fragments were cloned in a 3-piece ligation into the HindIII-XbaI sites of a pDZ vector to construct a recombinant vector pDZ-2lysA, in which 2 copies of argS/lysA were cloned in tandem. FIG. 5 is a map of the pDZ-2lysA vector.

The recombinant vector pDZ-2lysA was transformed into the lysine-producing *Corynebacterium glutamicum* KFCC10881-CJ3 prepared in Example 5, followed by the insertion of an additional copy of lysA gene just next to the lysA gene in the nuclear DNA through crossover so as to produce a lysine-producing strain anchoring two copies of lysA gene, which was named *Corynebacterium glutamicum* KFCC10881-CJ4. The adjacent positioning of two copies of lysA gene was determined through PCR using a set of primers (Table 9) designed to amplify a contact region between the two copies of lysA gene.

TABLE 9

| Primers | Base Sequences | SEQ ID NOS. |
|---|---|---|
| 2/ysAR | GAGATC AGC TGGTGT CAT GG | 23 |
| 2/ysAF5 | ATC CAC AGC GAA CTG GGC G | 24 |

The lysine-producing strain *Corynebacterium glutamicum* KFCC10881-CJ4, which anchors the six genes responsible for lysine biosynthesis in vivo, were deposited with the Korean Culture Center of Microorganisms on Aug. 21, 2006 under the accession number KCCM10770P.

EXAMPLE 7

Cloning of Lysine-Producing *Corynebacterium glutamicum* KFCC-10881-Derived pycGene, Construction of Recombinant Vector (pDZ-2pyc) and Preparation of Strain Anchoring pyc Information on the base sequence (NCBI Registration No. NC_003450, Ncg10659) of pyc gene was acquired from data of the NIH GenBank and used to design two pairs of primers to amplify a pyc gene ranging from the promoter region to the terminator codon (Table 10) in a manner similar to that of Example 3.

TABLE 10

| Primers | Base Sequences | SEQ ID NOS. |
|---|---|---|
| pyc-XbaI-F | ggc tct aga agg att gct ttg tgc act cct g | 31 |
| pyc-EcoRV-R | gaa gat atc gag cct tgg tct cca tct tc | 32 |
| pyc-EcoRV-F | gaa gat atc agg att gct ttg tgc act cct g | 33 |
| pyc-HindIII-R | gac aag ctt gag cct tgg tct cca tct tc | 34 |

PCR was performed using the nuclear DNA of *Corynebacterium glutamicum* KFCC10881 as a template and a set of oligonucleotide SEQ ID NOS. 31 and 32 or SEQ ID NOS. 33 and 34 as primers in the presence of PfuUltra™ High-Fidelity DNA Polymerase (Stratagene), with 30 cycles of denaturing at 96° C. for 30 sec, annealing at 52° C. for 30 sec, and extending at 72° C. for 4 min. The PCR products thus obtained were found to be two kinds of pyc genes, pyc-A and pyc-B, each containing a 3,925 bp-long promoter region, which were produced respectively with a set of SEQ ID NOS. 31 and 32 and a set of SEQ ID NOS. 33 and 34. The PCR products were cloned into the *E. coli* vector pCR2.1 with the aid of a TOPO Cloning Kit (Invitrogen) to give recombinant vectors pCR-pyc-A and pCR-pyc-B.

Figure 6:
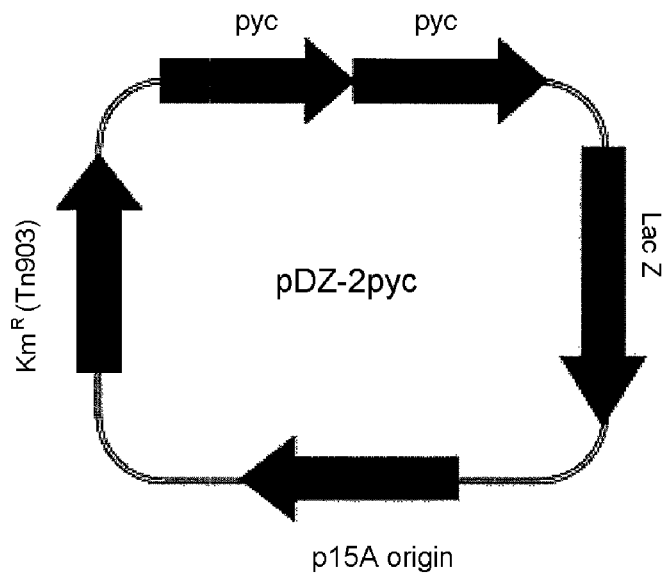
FIG. 6 is a schematic view showing a vector pDZ-2pyc for a nuclear-targeted gene into *Corynebacterium*.

These pCR vectors were treated with corresponding restriction enzymes, which are specific for opposite ends of pyc-A and pyc-B (pyc-A: XbaI and EcoRV, pyc-B: EcoRV and HindIII) to separate the pyc genes from the pCR vectors. These fragments were cloned in a 3-piece ligation into the XbaI-HindIII sites of a pDZ vector to construct a recombinant vector pDZ-2pyc, in which 2 copies of pyc were cloned in tandem. FIG. 6 is a map of the pDZ-2pyc vector.

The recombinant vector pDZ-2pyc was transformed into the lysine-producing *Corynebacterium glutamicum* KFCC10881-CJ4, prepared in Example 6, followed by the insertion of an additional copy of pycA gene just next to the pycA gene in the nuclear DNA through crossover so as to produce a lysine-producing strain anchoring two copies of pyc gene, which was named *Corynebacterium glutamicum* KFCC10881-CJ5. The adjacent positioning of two copies of pyc gene was determined through PCR using a set of primers (Table 11) designed to amplify the contact region between the two copies of pyc gene.

TABLE 11

| Primers | Base Sequences | SEQ ID NOS. |
|---|---|---|
| 2pyc-F | ctg agg aag agc agg cgc acc tcg | 35 |
| 2pyc-R | ttc cgc aca ctc gcg ggc aag ctg | 36 |

As a result, the lysine-producing strain *Corynebacterium glutamicum* KFCC10881-CJ5 anchors the seven genes involved in lysine biosynthesis.

EXAMPLE 8

Production of Lysine from Strains Anchoring Genes Responsible for Lysine-Biosynthesis The L-lysine-producing strains *Corynebacterium glutamicum* KFCC-10881-CJ4 and KFCC-10881-CJ5, which were prepared respectively in Examples 6 and 7, were cultured in order to produce L-lysine as follows.

*Corynebacterium glutamicum* KFCC-10881, KFCC-10881-CJ4 and KFCC-10881-CJ5 were inoculated into 240 ml-corner baffle flasks containing 25 ml of the following seed medium and cultured at 30° C. for 20 hour with shaking at 200 rpm. Thereafter, 1 ml of each of the cultures was inoculated into a 250 ml-corner baffle flask containing 24 ml of the following production medium and cultured at 30° C. for 120 hours with shaking at 200 rpm. The seed medium and the production medium comprise the following compositions.

Seed Medium (pH 7.0)

Glucose 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100☐, thiamine HCl 1000☐, calcium pantothenate 2000☐, nicotinamide 2000☐ (in 1 liter of distilled water)

Production Medium (pH 7.0)

glucose 100 g, $(NH_4)_2SO_4$ 40 g, soy protein 2.5 g, corn steep solids 5 g, urea 3 g, $KH_2PO_4$ 1 g, $MgSO_4$ $7H_2O$ 0.5 g, biotin 100☐, thiamine chloride 1000☐, calcium pantothenate 2000☐, nicotinamide 3000☐, and $CaC_3O$ 30 g (in 1 liter of distilled water).

After the completion of culture, HPLC analysis was performed to determine the amounts of the L-lysine produced by the strains. The concentrations of L-lysine in the cultures of *Corynebacterium glutamicum* KFCC10881, KFCC10881-CJ4 and KFCC10881-CJ5 are summarized in Table 12, below.

TABLE 12

| Strains | Lysine (g/l) | | |
|---|---|---|---|
| | Batch 1 | Batch 2 | Batch 3 |
| KFCC-10881 | 44 | 43 | 42.8 |
| KFCC-10881-CJ4 | 47 | 46.2 | 45.6 |
| KFCC-10881-CJ5 | 47.5 | 46.9 | 46.1 |

As seen in Table 12, *Corynebacterium glutamicum* KFCC-10881-CJ4, in which the six genes involved in lysine biosynthesis are anchored, was found to increase in lysine productivity by about 7%, compared with the mother strain KFCC-10881. Also, it was measured that an increase of about 8% in lysine production was obtained with *Corynebacterium glutamicum* KFCC-10881-CJ5, which anchors a pyc gene in addition to the six lysine biosynthesis genes, in comparison to the mother strain KFCC-10881.

EXAMPLE 9

Preparation of Lysine-Producing *Corynebacterium glutamicum* KFCC-10881-Derived Strain Anchoring Three Copies of lysC/asd Gene The recombinant vector pDZ-2lysC/asd, prepared in Example 4, was transformed into the lysine-producing *Corynebacterium glutamicum* KFCC10881-CJ4 prepared in Example 6, followed by the insertion of an additional copy of the lysC/asd gene just next to the two adjacent copies of the lysC/asd gene in the nuclear DNA through crossover so as to produce a lysine-producing strain anchoring three copies of the lysC/asd gene, which was named *Corynebacterium glutamicum* KFCC10881-CJ6. The alignment of three copies of the lysC/asd gene in tandem was determined through PCR using a set of primers (Table 13) designed to amplify contact regions among the three copies of the lysC/asd gene.

TABLE 13

| Primers | Base Sequences | SEQ ID NOS. |
|---|---|---|
| 3lysC-F | ggg cga att ctg cag at | 38 |
| 3lysC-R | atc tgc aga att cgc cc | 39 |

The lysine-producing strain *Corynebacterium glutamicum* KFCC10881-CJ6 was found to have aspartate kinase activity 2.1 times as high as that of KFCC10881-CJ4, as measured by the method using aspartyl hydroxamate according to Pechere J. F. and Capony J. P. (Anal Biochem 22: 536-539, 1968) (Table 14).

TABLE 14

| Strains | Aspartate Kinase Activity (Fold) |
|---|---|
| KFCC10881-CJ4 | 1 |
| KFCC10881-CJ6 | 2.1 |

EXAMPLE 10

Preparation of Lysine-Producing *Corynebacterium glutamicum* KFCC-10881-Derived Strain Anchoring Three Copies of dapA/dapB Gene The recombinant vector pDZ-2dapA/dapB, prepared in Example 5, was transformed into the lysine-producing Corynebacterium glutamicum KFCC10881-CJ6 prepared in Example 9, followed by the insertion of an additional copy of dapA/dapB gene just next to the two adjacent copies of dapA/dapB gene in the nuclear DNA through crossover so as to produce a lysine-producing strain anchoring three copies of dapA/dapB gene, which was named Corynebacterium glutamicum KFCC10881-CJ7. The alignment of three copies of dapA/dapB gene in tandem was determined through PCR using a set of primers (Table 15) designed to amplify contact regions among the three copies of dapA/dapB gene.

TABLE 15

| Primers | Base Sequences | SEQ ID NOS. |
|---|---|---|
| 3lysC-F | aaa cgc caa tga gag ctc tca | 40 |
| 3lysC-R | ctt ggc gct tgt gag ctc tga | 41 |

EXAMPLE 11

Lysine Production from the Strain Anchoring Complex Genes Responsible for Lysine Biosynthesis The L-lysine-producing strain Corynebacterium glutamicum KFCC-10881-CJ7, prepared in Example 10, was cultured to produce L-lysine as follows.

Corynebacterium glutamicum KFCC-10881-CJ4 and KFCC-10881-CJ7 were inoculated into 250 ml-corner baffle flasks, containing 25 ml of the following seed medium, and were cultured at 30° C. for 20 hour with shaking at 200 rpm. Thereafter, 1 ml of each of the cultures was inoculated into a 250 ml-corner baffle flask, containing 24 ml of the following production medium, and was cultured at 30° C. for 120 hours with shaking at 200 rpm. The seed medium and the production medium comprise the following compositions.

Seed Medium (pH 7.0)

glucose 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100☐, thiamine HCl 1000☐, calcium pantothenate 2000☐, nicotinamide 2000☐ (in 1 liter of distilled water)

Production Medium (pH 7.0)

glucose 100 g, $(NH_4)_2SO_4$ 40 g, soy protein 2.5 g, corn steep solids 5 g, urea 3 g, $KH_2PO_4$ 1 g, $MgSO_4$ $7H_2O$ 0.5 g, biotin 100☐, thiamine chloride 1000☐, calcium pantothenate 2000☐, nicotinamide 3000☐, $CaC_3O$ 30 g (in 1 liter of distilled water).

After the completion of culture, HPLC analysis was performed to determine the amounts of the L-lysine produced by the strains. The concentrations of L-lysine in the cultures of Corynebacterium glutamicum KFCC-10881-CJ4 and KFCC-10881-CJ7 are summarized in Table 16, below.

TABLE 16

| | Lysine (g/l) | | |
|---|---|---|---|
| Strains | Batch 1 | Batch 2 | Batch 3 |
| KFCC-10881-CJ4 | 46.4 | 46.8 | 45.9 |
| KFCC-10881-CJ7 | 51.8 | 51.2 | 51.7 |

As seen in Table 16, Corynebacterium glutamicum KFCC-10881-CJ7, in which the three genes involved in lysine biosynthesis are anchored in triplicate, was found to increase in lysine productivity by about 11%, compared with the mother strain KFCC-10881-CJ4.

EXAMPLE 12

Construction of Vector for Promoter Replacement and Preparation of Strain Replaced Exogenous Promoter for Lysine Biosynthesis Gene An exogenous potent CJ7 promoter was substituted for the native promoter for the lysine biosynthesis genes on the basis of pDZ. The CJ7 promoter is a strong, Corynebacterium ammoniagenes-derived promoter having a base sequence represented by SEQ ID NOS. 44 to 50. It is disclosed in Korean Pat. No. 0620092, issued to the present applicant. When the nuclear lysC of Corynebacterium glutamicum KFCC-10881 was expressed in the presence of the CJ7 promoter, aspartate kinase activity was found to increase by a multiple as high as 2 when using the inherent promoter.

A vector for introducing the CJ7 promoter into the nuclear DNA of the lysine-producing strains was prepared as follows.

Figure 7:
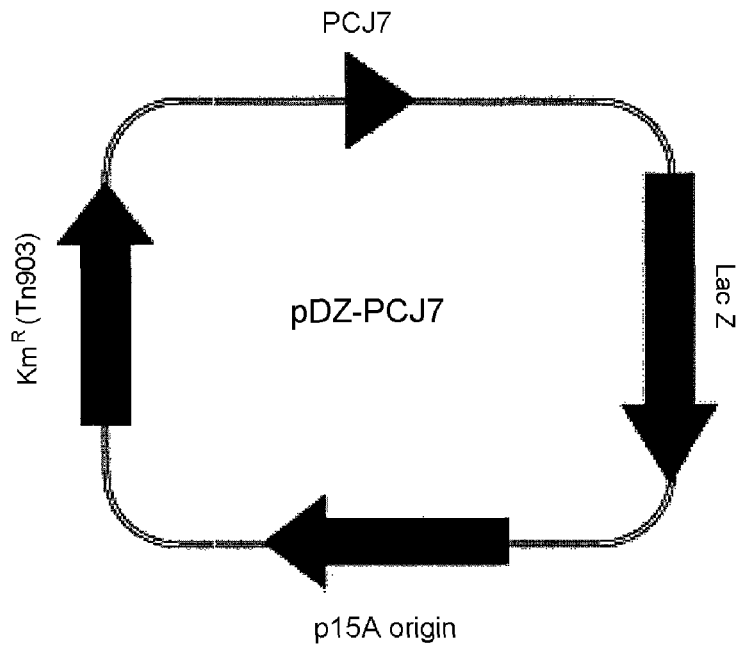
FIG. 7 is a schematic view showing a vector pDZ-PCJ7.
Figure 8:
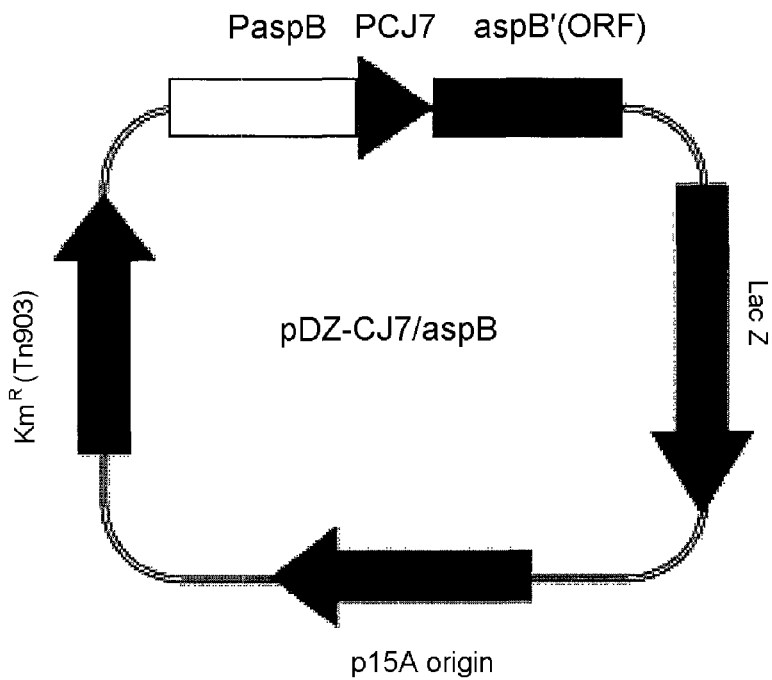
FIG. 8 is a schematic view showing a vector pDZ-PCJ7/aspB.
Figure 9:
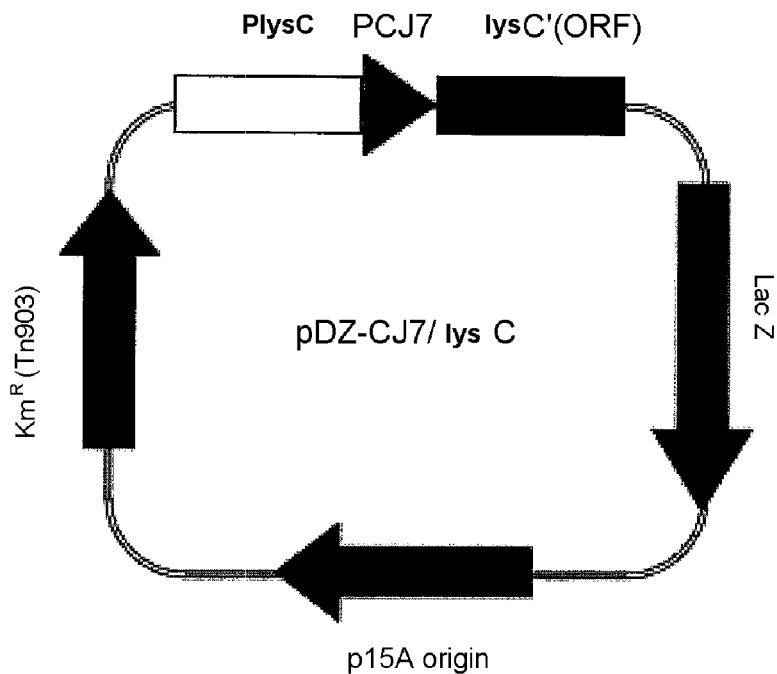
FIG. 9 is a schematic view showing a vector pDZ-PCJ7/lysC.
Figure 10:
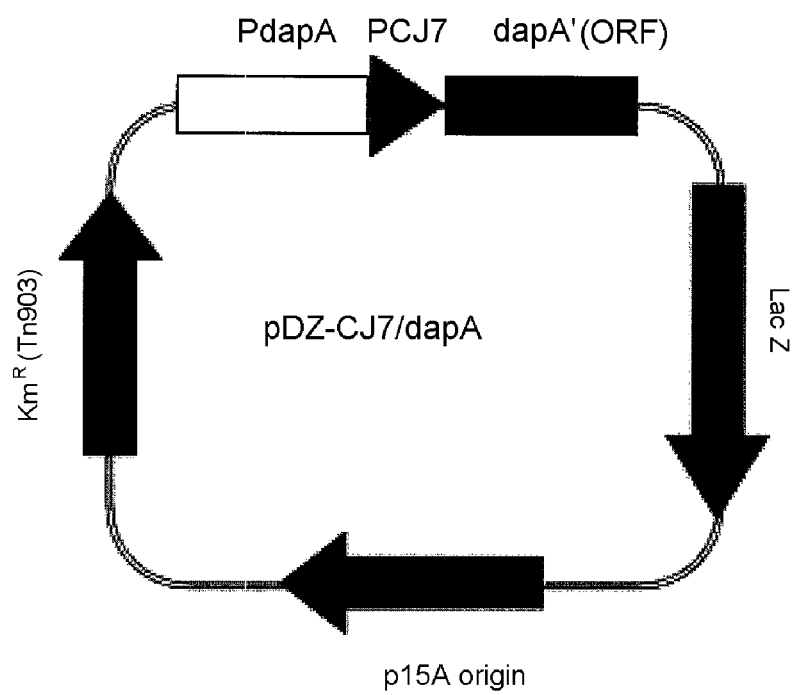
FIG. 10 is a schematic view showing a vector pDZ-PCJ7/dapA.
Figure 11:
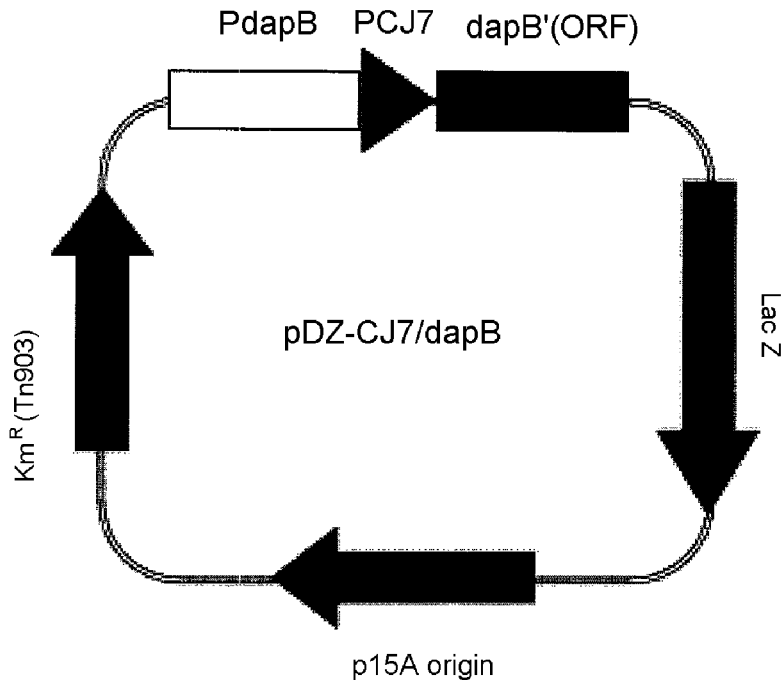
FIG. 11 is a schematic view showing a vector pDZ-PCJ7/dapB.
Figure 12:
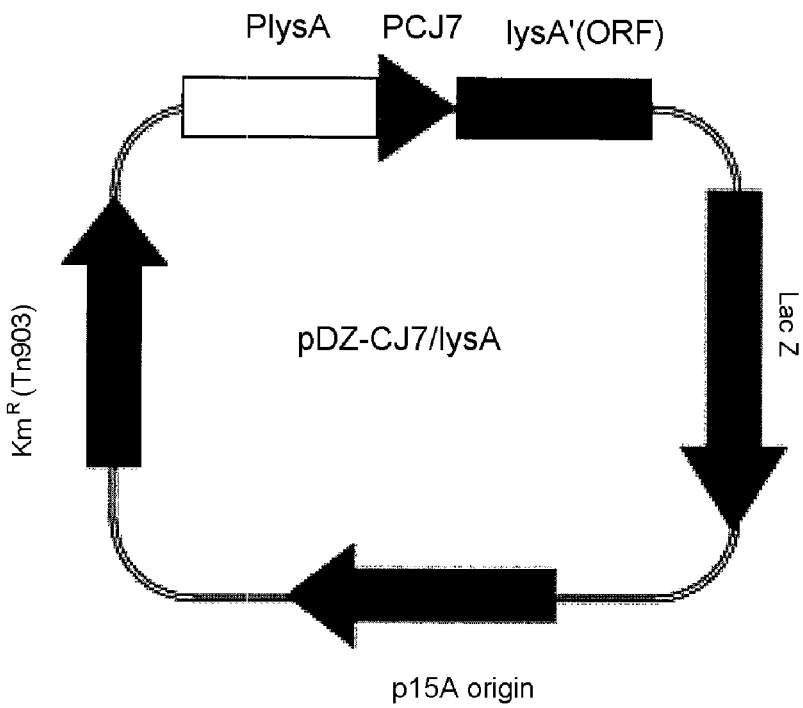
FIG. 12 is a schematic view showing a vector pDZ-PCJ7/lysA.
Figure 13:
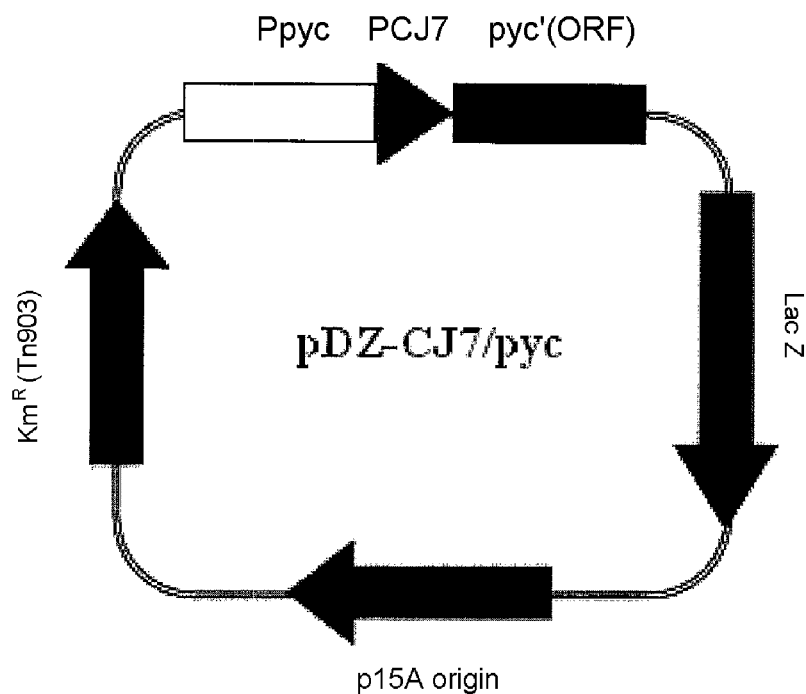
FIG. 13 is a schematic view showing a vector pDZ-PCJ7/pyc.

First, a pDZ vector was treated with restriction enzymes XbaI and NdeI. PCR was performed in the presence of SEQ ID NOS. 42 and 43 (Table 17) as primers designed to insert XbaI and NdeI sites respectively at the 5'- and the 3'-end of a PCR product amplified from the CJ7 promoter of the nuclear DNA of Corynebacterium ammoniagenes. After treatment with XbaI and NdeI, the CJ7 promoter PCR product was ligated to the truncated pDZ vector to give a pDZ-PCJ7 vector, which served as a primary plasmid for introducing a CJ7 promoter into the nuclear DNA of the strain (FIG. 7)

TABLE 17

| Primers | Base Sequences | SEQ ID NOS. |
|---|---|---|
| PCJ7-F-XbaI | tct agaaga aac atc cca gcg cta c | 42 |
| PCJ7-R-NdeI | cat atggag tgt ttc ctt tcg ttg | 43 |

PCR was performed, with the nuclear DNA of the lysine-producing strain Corynebacterium glutamicum KFCC10881 prepared in Example 2 serving as a template, to obtain two kinds of DNA fragments necessary for the substitution of the CJ7 promoter for respective native promoters of the genes introduced to the nuclear DNA, that is, a partial native promoter fragment about 300 bp long and a partial ORF about 300 bp long stretching from base +2 in the downstream direction. The primers used for the PCR were designed such that an XbaI site was inserted at opposite ends of the PCR product of the partial native promoter fragment and an NdeI site was inserted at opposite ends of the PCR product of the partial ORF. These PCR products were treated with respective restriction enzymes. pDZ-PCJ7 was digested with XbaI for ligation to the truncated PCR product of the partial native promoter fragment and then with NdeI for ligation to the truncated PCR production of the partial ORF to construct recombinant plasmids, respectively named pDZ-PCJ7-aspB, pDZ-PCJ7-lysCasd, pDZ-PCJ7-dapA, pDZ-PCJ7-dapB, pDZ-PCJ7-argSlysA and pDZ-PCJ7-pyc, each comprising a CJ7 promoter located between the two PCR DNA fragments (FIGS. 8 to 13).

The plasmids were used for the recombination of target genes as follows. First, the recombinant vector pDZ-PCJ7-aspB was transformed into the lysine-producing Corynebacterium glutamicum KFCC-10881, which then underwent crossover to the CJ7 promoter at the promoter region of the aspB gene in the nuclear DNA. In the same way, the other recombinant plasmids were transformed in order to create a novel strain KFCC-10881-PCJ7-5 in which a CJ7 promoter is located at the promoter regions of aspB, lysCasd, dapA, dapB and argSlysA genes. In addition to the promoters, the promoter of the pyc gene was substituted with a CJ7 promoter to create KFCC-10881-PCJ7-6.

EXAMPLE 13

Production of Lysine in Strain Having Exogenous Promoter for Lysine Biosynthesis Gene The L-lysine-producing strains *Corynebacterium glutamicum* KFCC-10881-PCJ7-5 and KFCC-10881-PCJ7-6 were cultured to produce L-lysine as follows.

*Corynebacterium glutamicum* KFCC-10881, KFCC-10881-PCJ7-5 and KFCC-10881-PCJ7-6 were inoculated into 250 ml-corner baffle flasks containing 25 ml of the following seed medium, and were cultured at 30° C. for 20 hours with shaking at 200 rpm. Thereafter, 1 ml of each of the cultures was inoculated into a 250 ml-corner baffle flask containing 24 ml of the following production medium and cultured at 30° C. for 120 hours with shaking at 200 rpm. The seed medium and the production medium comprise the following compositions.

Seed Medium (pH 7.0)

glucose 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100□, thiamine HCl 1000□, calcium pantothenate 2000□, nicotinamide 2000□ (in 1 liter of distilled water)

Production Medium (pH 7.0)

glucose 100 g, $(NH_4)_2SO4$ 40 g, soy protein 2.5 g, corn steep solids 5 g, urea 3 g, $KH_2PO4$ 1 g, $MgSO_4$ $7H_2O$ 0.5 g, biotin 100□, thiamine chloride 1000□, calcium pantothenate 2000□, nicotinamide 3000□, $CaC_3O$ 30 g (in 1 liter of distilled water).

After the completion of culture, HPLC analysis was performed to determine the amounts of the L-lysine produced by the strains. The concentrations of L-lysine in the cultures of *Corynebacterium glutamicum* KFCC-10881, KFCC-10881-PCJ7-5 and KFCC-10881-PCJ7-6 are summarized in Table 18, below.

TABLE 18

| Strains | Lysine (g/l) | | |
|---|---|---|---|
| | Batch 1 | Batch 2 | Batch 3 |
| KFCC-10881 | 43.5 | 44.2 | 43.8 |
| KFCC-10881-PCJ7-5 | 51.4 | 51.8 | 51.1 |
| KFCC-10881-PCJ7-6 | 52 | 52.1 | 51.7 |

As seen in Table 18, *Corynebacterium glutamicum* KFCC-10881-PCJ7-5, in which the six genes involved in lysine biosynthesis were anchored along with respective exogenous CJ7 promoters therefor and *Corynebacterium glutamicum* KFCC-10881-PCJ7-6, in which a pyc gene and a CJ7 promoter therefor were anchored in addition to the six genes and promoters, were found to increase in lysine productivity by about 17.4% and 18.6% respectively, compared with the mother strain KFCC-10881.

EXAMPLE 14

Activity of Lysine Biosynthesis Enzymes in Strain Anchoring Additional Gene Responsible for Lysine Biosynthesis and Having Replaced Exogenous Promoter Therefor The L-lysine-producing strains *Corynebacterium glutamicum* KFCC10881-CJ4, KFCC10881-CJ7 and KFCC-10881-PCJ7-5, prepared respectively in Examples 6, 10 and 12, were assayed for the activity of aspartate kinase and diaminopimelate decarboxylase as representatives of lysine biosynthesis enzymes because their activity is relatively easy to measure. The modified lysine-producing strains were found to increase in enzyme activity compared to the initial mother strain KFCC10881 (Table 19) as measured by the method according to Pechere J. F. and Capony J. P. (Anal Biochem 22: 536-539, 1968) for aspartate kinase activity and the method according to J. Cremer et al. for diaminopimelate decarboxylase activity.

TABLE 19

| Strains | Enzyme Activity (Fold) | |
|---|---|---|
| | Aspartate kinase | Diaminopimelate decarboxylase |
| KFCC-10881 | 1 | 1 |
| KFCC-10881-CJ4 | 1.7 | 1.8 |
| KFCC-10881-CJ6 | 3.2 | 1.9 |
| KFCC-10881-PCJ7-5 | 2.3 | 5.8 |

The invention claimed is:

1. A modified *Corynebacteria* microorganism, in which the following genes are overexpressed compared to respective endogenous expression thereof, wherein the genes are involved in lysine production, and wherein the overexpressed genes in the microorganism consist essentially of:
a gene encoding aspartate aminotransferase;
a gene encoding aspartate kinase;
a gene encoding aspartate semialdehyde dehydrogenase;
a gene encoding dihydrodipicolinate synthase;
a gene encoding dihydropicolinate reductase; and
a gene encoding diaminopimelate decarboxylase.

2. The *Corynebacteria* microorganism as set forth in claim 1, wherein
the gene encoding aspartate aminotransferase is an aspB gene of a coryneform bacteria;
the gene encoding aspartate kinase is a lysC gene of a coryneform bacteria;
the gene encoding aspartate semialdehyde dehydrogenase is an asd gene of a coryneform bacteria;
the gene encoding dihydrodipicolinate synthase is a dapA gene of a coryneform bacteria;
the gene encoding dihydropicolinate reductase is a dapB gene of a coryneform bacteria; and
the gene encoding diaminopimelate dicarboxylase is a lysA gene of a coryneform bacteria.

3. The *Corynebacteria* microorganism as set forth in claim 2, wherein the microorganism comprises one or more exogenous copies of:
the gene encoding aspartate aminotransferase;
the gene encoding aspartate kinase;
the gene encoding aspartate semialdehyde dehydrogenase;
the gene encoding dihydrodipicolinate synthase;
the gene encoding dihydropicolinate reductase; and
the gene encoding diaminopimelate decarboxylase.

4. The *Corynebacteria* microorganism as set forth in claim 3, wherein the one or more exogenous copies of the genes are integrated in nuclear DNA of the microorganism.

5. The *Corynebacteria* microorganism as set forth in claim 2, wherein the aspB gene comprises a nucleotide sequence of SEQ ID NO. 25.

6. The *Corynebacteria* microorganism as set forth in claim 2, wherein each of the following genes comprises a promoter more potent than its endogenous promoter:
the gene encoding aspartate aminotransferase;
the gene encoding aspartate kinase;
the gene encoding aspartate semialdehyde dehydrogenase;
the gene encoding dihydrodipicolinate synthase;
the gene encoding dihydropicolinate reductase; and
the gene encoding diaminopimelate decarboxylase.

7. The *Corynebacteria* microorganism as set forth in claim 6, wherein the promoter for each of the genes comprises a nucleotide sequence selected from SEQ ID NOS. 44 to 50.

8. The *Corynebacteria* microorganism as set forth in claim 7, wherein the promoter for each of the genes is a nucleotide sequence of SEQ ID NO. 44.

9. The *Corynebacteria* microorganism as set forth in claim 6, wherein the promoter for each of the genes is introduced by transforming a coryneform bacteria with at least one of the vectors of FIGS. 8 to 13.

10. The *Corynebacteria* microorganism as set forth in claim 2, wherein the lysC gene comprises a nucleotide sequence of SEQ ID NO. 26.

11. The *Corynebacteria* microorganism as set forth in claim 2, wherein the asd gene comprises a nucleotide sequence of SEQ ID NO. 27.

12. The *Corynebacteria* microorganism as set forth in claim 2, wherein the dapA gene comprises a nucleotide sequence of SEQ ID NO. 28.

13. The *Corynebacteria* microorganism as set forth in claim 2, wherein the dapB gene comprises a nucleotide sequence of SEQ ID NO. 29.

14. The *Corynebacteria* microorganism as set forth in claim 2, wherein the lysA gene comprises a nucleotide sequence of SEQ ID NO. 30.

15. A method of producing L-lysine, comprising:
culturing the *Corynebacteria* microorganism of claim 1; and
recovering lysine from cells of the microorganism or culture media.

16. A modified *Corynebacteria* microorganism, in which the following genes are overexpressed compared to respective endogenous expression thereof, wherein the genes are involved in lysine production, and wherein the overexpressed genes in the microorganism consist essentially of:
a gene encoding aspartate aminotransferase;
a gene encoding aspartate kinase;
a gene encoding aspartate semialdehyde dehydrogenase;
a gene encoding dihydrodipicolinate synthase;
a gene encoding dihydropicolinate reductase;
a gene encoding diaminopimelate decarboxylase; and
a gene encoding pyruvate carboxylase.

17. The *Corynebacteria* microorganism as set forth in claim 16, wherein
the gene encoding aspartate aminotransferase is an aspB gene of a coryneform bacteria;
the gene encoding aspartate kinase is a lysC gene of a coryneform bacteria;
the gene encoding aspartate semialdehyde dehydrogenase is an asd gene of a coryneform bacteria;
the gene encoding dihydrodipicolinate synthase is a dapA gene of a coryneform bacteria;
the gene encoding dihydropicolinate reductase is a dapB gene of a coryneform bacteria;
the gene encoding diaminopimelate dicarboxylase is a lysA gene of a coryneform bacteria; and
the gene encoding pyruvate carboxylase is a pyc gene of a coryneform bacteria.

18. The *Corynebacteria* microorganism as set forth in claim 17, wherein the pyc gene comprises a nucleotide sequence of SEQ ID NO. 37.

19. The *Corynebacteria* microorganism as set forth in claim 16, wherein the microorganism comprises one or more exogenous copies of:
the gene encoding aspartate aminotransferase;
the gene encoding aspartate kinase;
the gene encoding aspartate semialdehyde dehydrogenase;
the gene encoding dihydrodipicolinate synthase;
the gene encoding dihydropicolinate reductase;
the gene encoding diaminopimelate decarboxylase; and
the gene encoding pyruvate carboxylase.

20. The *Corynebacteria* microorganism as set forth in claim 16, wherein each of the following genes comprises a promoter more potent than its endogenous promoter:
- the gene encoding aspartate aminotransferase;
- the gene encoding aspartate kinase;
- the gene encoding aspartate semialdehyde dehydrogenase;
- the gene encoding dihydrodipicolinate synthase;
- the gene encoding dihydropicolinate reductase;
- the gene encoding diaminopimelate decarboxylase; and
- the gene encoding pyruvate carboxylase.

21. A method of producing L-lysine, comprising:
- culturing the *Corynebacteria* microorganism of claim 16; and
- recovering lysine from cells of the microorganism or culture media.

22. *Corynebacterium glutamicum* KFCC10881-CJ4 having accession number KCCM10770P.

* * * * *